(12) United States Patent
Korb et al.

(10) Patent No.: US 10,376,273 B2
(45) Date of Patent: *Aug. 13, 2019

(54) METHODS AND APPARATUSES FOR TREATMENT OF MEIBOMIAN GLANDS

(71) Applicant: TearScience, Inc., Morrisville, NC (US)

(72) Inventors: Donald R. Korb, Boston, MA (US); Timothy R. Willis, Raleigh, NC (US); Stephen M. Grenon, Durham, NC (US)

(73) Assignee: TearScience, Inc., Morrisville, NC (US)

( * ) Notice: Subject to any disclaimer, the term of this patent is extended or adjusted under 35 U.S.C. 154(b) by 1203 days.

This patent is subject to a terminal disclaimer.

(21) Appl. No.: 14/510,863

(22) Filed: Oct. 9, 2014

(65) Prior Publication Data

US 2015/0100063 A1    Apr. 9, 2015

Related U.S. Application Data

(63) Continuation of application No. 13/183,901, filed on Jul. 15, 2011, now Pat. No. 9,216,028, which is a
(Continued)

(51) Int. Cl.
*A61F 7/00*    (2006.01)
*A61F 7/02*    (2006.01)
(Continued)

(52) U.S. Cl.
CPC .......... *A61B 17/22004* (2013.01); *A61F 7/02* (2013.01); *A61F 9/00772* (2013.01);
(Continued)

(58) Field of Classification Search
None
See application file for complete search history.

(56) References Cited

U.S. PATENT DOCUMENTS 168,352 A    10/1875   Sloan
1,006,945 A  10/1911   Houston
(Continued)

FOREIGN PATENT DOCUMENTS

AU    2011302478 A1    3/2013
CA    2331257 A1       11/1999
(Continued)

OTHER PUBLICATIONS

Non-Final Office Action for U.S. Appl. No. 11/931,914, dated Jun. 8, 2015, 25 pages.
(Continued)

*Primary Examiner* — Kaitlyn E Smith
(74) *Attorney, Agent, or Firm* — Withrow & Terranova, P.L.L.C.

(57) ABSTRACT

Methods and apparatuses of treating meibomian glands are disclosed. The method comprises applying regulated heat to an eyelid to reach a temperature adequate to melt at least one obstruction within at least one meibomian gland. The method also comprises maintaining the regulated heat for a time period adequate to place the at least obstruction in the melted state. The method further comprises positioning a pressure application device into contact with the patient's eyelid and applying a pressure with the pressure application device over a substantial portion of the eyelid to express the at least one obstruction from the meibomian gland. An apparatus suitable to treat meibomian glands comprises a heater, a controller, and a pressure applicator configured to be placed into contact with the eyelid and apply a pressure over a substantial portion of the eyelid to express the at least one obstruction from the meibomian gland.

15 Claims, 13 Drawing Sheets

Related U.S. Application Data continuation of application No. 11/541,418, filed on Sep. 29, 2006, now Pat. No. 7,981,145, which is a continuation-in-part of application No. 11/434,054, filed on May 15, 2006, now Pat. No. 8,083,787, which is a continuation-in-part of application No. 11/434,033, filed on May 15, 2006, now Pat. No. 8,915,253, and a continuation-in-part of application No. 11/434,446, filed on May 15, 2006, now abandoned.

(60) Provisional application No. 60/700,233, filed on Jul. 18, 2005.

(51) Int. Cl.
*A61H 7/00* (2006.01)
*A61N 7/00* (2006.01)
*A61B 17/22* (2006.01)
*A61B 18/04* (2006.01)
*A61B 18/12* (2006.01)
*A61F 9/007* (2006.01)
*A61H 15/00* (2006.01)

(52) U.S. Cl.
CPC .............. *A61H 7/00* (2013.01); *A61B 18/12* (2013.01); *A61B 2018/046* (2013.01); *A61B 2018/048* (2013.01); *A61F 2007/0004* (2013.01); *A61F 2007/0059* (2013.01); *A61H 2015/0014* (2013.01); *A61N 7/00* (2013.01)

(56) References Cited

U.S. PATENT DOCUMENTS

| | | |
|---|---|---|
| 1,924,315 A | 8/1933 | Hemphill et al. |
| 2,545,724 A | 3/1951 | Curtis |
| 2,891,252 A | 6/1959 | Lazo |
| 3,140,390 A | 7/1964 | Smith et al. |
| 3,333,586 A | 8/1967 | Bellis et al. |
| 3,404,678 A | 10/1968 | Von Ardenne |
| 3,415,299 A | 12/1968 | Hinman, Jr. et al. |
| 3,667,476 A | 6/1972 | Muller |
| 3,915,346 A | 10/1975 | Allsop |
| 3,952,735 A | 4/1976 | Wirtschafter et al. |
| 4,069,084 A | 1/1978 | Mlodozeniec et al. |
| 4,131,115 A | 12/1978 | Peng |
| 4,261,364 A | 4/1981 | Haddad et al. |
| 4,387,707 A | 6/1983 | Polikoff |
| 4,612,959 A | 9/1986 | Costello |
| 4,778,457 A | 10/1988 | York |
| 4,883,454 A | 11/1989 | Hamburg |
| 4,914,088 A | 4/1990 | Glonek et al. |
| 4,918,818 A | 4/1990 | Hsieh |
| 4,955,377 A | 9/1990 | Lennox et al. |
| 4,958,632 A | 9/1990 | Duggan |
| 5,020,455 A | 6/1991 | Takashi et al. |
| 5,030,214 A | 7/1991 | Spector |
| 5,097,829 A | 3/1992 | Quisenberry |
| 5,151,100 A | 9/1992 | Abele et al. |
| 5,158,082 A | 10/1992 | Jones |
| 5,169,384 A | 12/1992 | Bosniak et al. |
| 5,213,097 A | 5/1993 | Zeindler |
| 5,251,627 A | 10/1993 | Morris |
| 5,283,063 A | 2/1994 | Freeman |
| 5,314,456 A | 5/1994 | Cohen |
| 5,327,886 A | 7/1994 | Chiu |
| 5,343,561 A | 9/1994 | Adamo |
| D352,106 S | 11/1994 | Fanney et al. |
| 5,368,582 A | 11/1994 | Bertera |
| 5,368,591 A | 11/1994 | Lennox et al. |
| 5,377,701 A | 1/1995 | Fang |
| 5,419,772 A | 5/1995 | Teitz et al. |
| 5,425,380 A | 6/1995 | Hudson et al. |
| 5,496,311 A | 3/1996 | Abele et al. |
| 5,601,548 A | 2/1997 | Smith et al. |
| 5,628,772 A | 5/1997 | Russell |
| 5,643,336 A | 7/1997 | Lopez-Claros |
| 5,700,238 A | 12/1997 | Hyson |
| 5,720,773 A | 2/1998 | Lopez-Claros |
| 5,782,857 A | 7/1998 | Machuron |
| 5,795,312 A | 8/1998 | Dye |
| 5,807,357 A | 9/1998 | Kang |
| 5,836,927 A | 11/1998 | Fried |
| 5,893,719 A | 4/1999 | Radow |
| 5,958,912 A | 9/1999 | Sullivan |
| 5,960,608 A | 10/1999 | Ohtonen |
| 5,964,723 A | 10/1999 | Augustine |
| 6,007,501 A | 12/1999 | Cabados et al. |
| 6,024,095 A | 2/2000 | Stanley, III |
| 6,041,821 A | 3/2000 | Grossman |
| 6,107,289 A | 8/2000 | Sullivan |
| 6,110,292 A | 8/2000 | Jewett et al. |
| 6,112,900 A | 9/2000 | Adkins, Jr. |
| 6,113,561 A | 9/2000 | Augustine |
| 6,153,607 A | 11/2000 | Pflugfelder et al. |
| 6,155,995 A | 12/2000 | Lin |
| 6,181,970 B1 | 1/2001 | Kasevich |
| 6,193,740 B1 | 2/2001 | Rodriguez |
| 6,206,842 B1 | 3/2001 | Tu et al. |
| 6,213,966 B1 | 4/2001 | Augustine |
| 6,273,886 B1 | 8/2001 | Edwards et al. |
| 6,275,735 B1 | 8/2001 | Jarding et al. |
| 6,309,364 B1 | 10/2001 | Cathaud et al. |
| 6,312,397 B1 | 11/2001 | Gebhard |
| D456,079 S | 4/2002 | Fujii |
| 6,423,018 B1 | 7/2002 | Augustine |
| 6,425,888 B1 | 7/2002 | Embleton et al. |
| 6,436,128 B1 | 8/2002 | Usui |
| 6,438,398 B1 | 8/2002 | Pflugfelder et al. |
| 6,455,583 B1 | 9/2002 | Pflugfelder et al. |
| 6,482,203 B2 | 11/2002 | Paddock et al. |
| 6,490,488 B1 | 12/2002 | Rudie et al. |
| D472,637 S | 4/2003 | Cooper et al. |
| 6,544,193 B2 | 4/2003 | Abreu |
| 6,544,257 B2 | 4/2003 | Nagase et al. |
| D477,084 S | 7/2003 | Menezes et al. |
| 6,641,264 B1 | 11/2003 | Schwebel |
| 6,648,904 B2 | 11/2003 | Altshuler et al. |
| 6,706,001 B2 | 3/2004 | Fresco |
| 6,780,176 B2 | 8/2004 | Hasegawa |
| 6,788,977 B2 | 9/2004 | Fenn et al. |
| 6,827,898 B1 | 12/2004 | Fausset et al. |
| 6,840,954 B2 | 1/2005 | Dietz et al. |
| 6,860,852 B2 | 3/2005 | Schonenberger et al. |
| 6,860,880 B2 | 3/2005 | Treat et al. |
| 6,874,884 B2 | 4/2005 | Schwebel |
| 6,882,885 B2 | 4/2005 | Levy, Jr. et al. |
| 6,886,933 B2 | 5/2005 | Schwebel |
| 6,908,195 B2 | 6/2005 | Fuller |
| 6,925,317 B1 | 8/2005 | Samuels et al. |
| 6,974,454 B2 | 12/2005 | Hooven |
| 7,001,379 B2 | 2/2006 | Behl et al. |
| 7,004,942 B2 | 2/2006 | Laird et al. |
| 7,036,928 B2 | 5/2006 | Schwebel |
| 7,060,061 B2 | 6/2006 | Altshuler et al. |
| 7,069,084 B2 | 6/2006 | Yee |
| 7,108,694 B2 | 9/2006 | Miura et al. |
| 7,118,591 B2 | 10/2006 | Frank et al. |
| 7,122,013 B2 | 10/2006 | Liu |
| 7,122,047 B2 | 10/2006 | Grahn et al. |
| 7,123,968 B1 | 10/2006 | Casscells, III et al. |
| 7,211,070 B2 | 5/2007 | Soroudi |
| 7,229,468 B2 | 6/2007 | Wong et al. |
| 7,231,922 B2 | 6/2007 | Davison et al. |
| D546,459 S | 7/2007 | Banryu |
| D552,736 S | 10/2007 | Yamaoka |
| D553,750 S | 10/2007 | Yamaoka |
| 7,316,657 B2 | 1/2008 | Kleinhenz et al. |
| 7,357,500 B2 | 4/2008 | Schwebel |
| 7,384,405 B2 | 6/2008 | Rhoades |
| 7,442,174 B2 | 10/2008 | Butler |
| 7,513,893 B2 | 4/2009 | Soroudi |
| 7,559,907 B2 | 7/2009 | Krempel et al. |
| 7,594,728 B2 | 9/2009 | Seal et al. |

(56) References Cited

U.S. PATENT DOCUMENTS

| | | |
|---|---|---|
| 7,637,878 B2 | 12/2009 | Lin |
| D612,941 S | 3/2010 | Youngquist et al. |
| D614,774 S | 4/2010 | Gausmann et al. |
| 7,712,899 B2 | 5/2010 | Tanassi et al. |
| 7,976,573 B2 | 7/2011 | Korb et al. |
| 7,981,145 B2 * | 7/2011 | Korb .................. A61F 7/02 128/898 |
| 7,981,146 B2 | 7/2011 | Korb et al. |
| 7,981,147 B2 * | 7/2011 | Korb .................. A61F 7/12 128/898 |
| 8,007,524 B2 | 8/2011 | Korb et al. |
| D645,565 S | 9/2011 | Smith et al. |
| 8,025,689 B2 | 9/2011 | Korb et al. |
| 8,083,787 B2 | 12/2011 | Korb et al. |
| 8,128,673 B2 | 3/2012 | Korb et al. |
| 8,128,674 B2 | 3/2012 | Korb et al. |
| 8,137,390 B2 | 3/2012 | Korb et al. |
| 8,187,310 B2 | 5/2012 | Korb et al. |
| 8,187,311 B2 | 5/2012 | Korb et al. |
| 8,262,715 B2 | 9/2012 | Wong, Jr. et al. |
| 8,455,016 B2 | 6/2013 | Maskin |
| 8,617,229 B2 | 12/2013 | Korb et al. |
| 8,628,504 B2 | 1/2014 | Grenon et al. |
| 8,791,158 B2 | 7/2014 | Dalton et al. |
| 8,906,427 B2 | 12/2014 | Maskin |
| 8,925,484 B2 | 1/2015 | Maier, Jr. et al. |
| 8,950,405 B2 * | 2/2015 | Grenon .................. A61F 7/02 128/898 |
| 9,039,718 B2 | 5/2015 | Rynerson |
| 9,510,972 B2 | 12/2016 | Badawi |
| 9,763,827 B2 | 9/2017 | Kelleher et al. |
| 9,822,142 B2 | 11/2017 | Cavanagh et al. |
| 2001/0041886 A1 | 11/2001 | Durkin et al. |
| 2002/0013572 A1 | 1/2002 | Berlin |
| 2002/0035345 A1 | 3/2002 | Beck |
| 2002/0049374 A1 | 4/2002 | Abreu |
| 2002/0099094 A1 | 7/2002 | Anderson |
| 2002/0111608 A1 | 8/2002 | Baerveldt et al. |
| 2002/0128696 A1 | 9/2002 | Pearl et al. |
| 2002/0156402 A1 | 10/2002 | Woog et al. |
| 2003/0050594 A1 | 3/2003 | Zamierowski |
| 2003/0056281 A1 | 3/2003 | Hasegawa |
| 2003/0065277 A1 | 4/2003 | Covington |
| 2003/0073987 A1 | 4/2003 | Sakurai et al. |
| 2003/0088241 A1 | 5/2003 | Hasegawa |
| 2003/0100936 A1 | 5/2003 | Altshuler et al. |
| 2003/0114426 A1 | 6/2003 | Pflugfelder et al. |
| 2003/0139790 A1 | 7/2003 | Ingle et al. |
| 2003/0195438 A1 | 10/2003 | Petillo |
| 2003/0211043 A1 | 11/2003 | Korb |
| 2003/0233135 A1 | 12/2003 | Yee |
| 2004/0064169 A1 | 4/2004 | Briscoe et al. |
| 2004/0064171 A1 | 4/2004 | Briscoe et al. |
| 2004/0076695 A1 | 4/2004 | Gilbard |
| 2004/0111138 A1 | 6/2004 | Bleam et al. |
| 2004/0153093 A1 | 8/2004 | Donovan |
| 2004/0199158 A1 | 10/2004 | Hood et al. |
| 2004/0237696 A1 * | 12/2004 | Hilsky .................. B62K 23/06 74/501.6 |
| 2004/0237969 A1 | 12/2004 | Fuller |
| 2004/0249427 A1 | 12/2004 | Nabilsi |
| 2004/0260209 A1 | 12/2004 | Ella et al. |
| 2005/0022823 A1 | 2/2005 | Davison et al. |
| 2005/0119629 A1 | 6/2005 | Soroudi |
| 2005/0143798 A1 | 6/2005 | Bleam et al. |
| 2005/0187502 A1 | 8/2005 | Krempel et al. |
| 2005/0220742 A1 | 10/2005 | Breen |
| 2005/0234506 A1 | 10/2005 | Weser |
| 2006/0018953 A1 * | 1/2006 | Guillon .................. A61F 7/034 424/443 |
| 2006/0030604 A1 | 2/2006 | Elsinger et al. |
| 2006/0055878 A1 | 3/2006 | Yee |
| 2006/0069420 A1 | 3/2006 | Rademacher et al. |
| 2006/0104914 A1 | 5/2006 | Soroudi |
| 2006/0135890 A1 | 6/2006 | Tsai |
| 2006/0136022 A1 | 6/2006 | Wong, Jr. et al. |
| 2006/0139569 A1 | 6/2006 | Schwebel |
| 2006/0154901 A1 | 7/2006 | Pflugfelder et al. |
| 2006/0157064 A1 | 7/2006 | Davison et al. |
| 2006/0183698 A1 | 8/2006 | Abelson |
| 2006/0212101 A1 | 9/2006 | Cheng |
| 2006/0233859 A1 | 10/2006 | Whitcup et al. |
| 2007/0016254 A1 | 1/2007 | Grenon et al. |
| 2007/0016256 A1 | 1/2007 | Korb et al. |
| 2007/0027411 A1 | 2/2007 | Ella et al. |
| 2007/0049913 A1 | 3/2007 | Grenon et al. |
| 2007/0060988 A1 | 3/2007 | Grenon et al. |
| 2007/0106349 A1 | 5/2007 | Karni et al. |
| 2007/0129711 A1 | 6/2007 | Altshuler et al. |
| 2007/0173799 A1 | 7/2007 | Hsia |
| 2007/0203462 A1 | 8/2007 | Soroudi |
| 2007/0270760 A1 | 11/2007 | Dacquay et al. |
| 2007/0280924 A1 | 12/2007 | Daniels et al. |
| 2008/0051741 A1 | 2/2008 | Grenon et al. |
| 2008/0075787 A1 | 3/2008 | Hibino |
| 2008/0081999 A1 | 4/2008 | Gravely et al. |
| 2008/0114423 A1 | 5/2008 | Grenon et al. |
| 2008/0132973 A1 | 6/2008 | Lord et al. |
| 2008/0188839 A1 | 8/2008 | Chan et al. |
| 2008/0200848 A1 | 8/2008 | Avni |
| 2008/0221649 A1 | 9/2008 | Echague et al. |
| 2008/0251085 A1 | 10/2008 | Schwebel |
| 2009/0043365 A1 | 2/2009 | Friedland et al. |
| 2009/0137533 A1 | 5/2009 | Adkins, Jr. |
| 2009/0149930 A1 | 6/2009 | Schenck |
| 2009/0192478 A1 | 7/2009 | Soroudi |
| 2009/0306111 A1 | 12/2009 | Nakamura et al. |
| 2009/0306607 A1 | 12/2009 | Yasuhiro |
| 2010/0087899 A1 | 4/2010 | Erez et al. |
| 2010/0100029 A1 | 4/2010 | Maskin |
| 2010/0292630 A1 | 11/2010 | Maskin |
| 2011/0022010 A1 | 1/2011 | Grenon et al. |
| 2011/0039805 A1 | 2/2011 | Pflugfelder et al. |
| 2011/0059902 A1 | 3/2011 | Sullivan et al. |
| 2011/0059925 A1 | 3/2011 | Donnenfeld |
| 2011/0124725 A1 | 5/2011 | Maskin |
| 2011/0130729 A1 | 6/2011 | Korb et al. |
| 2011/0172302 A1 | 7/2011 | Dalton et al. |
| 2011/0203832 A1 | 8/2011 | Schrock |
| 2011/0251532 A1 | 10/2011 | Yang |
| 2011/0273550 A1 | 11/2011 | Amano et al. |
| 2011/0294897 A1 | 12/2011 | Aberg et al. |
| 2012/0003296 A1 | 1/2012 | Shantha et al. |
| 2012/0065556 A1 | 3/2012 | Smith et al. |
| 2012/0093876 A1 | 4/2012 | Ousler, III et al. |
| 2012/0109041 A1 | 5/2012 | Munz |
| 2012/0128763 A1 | 5/2012 | Maskin |
| 2012/0209154 A1 | 8/2012 | Williams, III et al. |
| 2012/0220612 A1 | 8/2012 | Nakamura et al. |
| 2012/0321673 A1 | 12/2012 | Ogawa et al. |
| 2013/0045927 A1 | 2/2013 | Dana et al. |
| 2013/0046367 A1 | 2/2013 | Chen |
| 2013/0053733 A1 | 2/2013 | Korb et al. |
| 2013/0065867 A1 | 3/2013 | Smith et al. |
| 2013/0110101 A1 | 5/2013 | Van Valen et al. |
| 2013/0131171 A1 | 5/2013 | Maskin |
| 2013/0172790 A1 | 7/2013 | Badawi |
| 2013/0172829 A1 | 7/2013 | Badawi |
| 2014/0330129 A1 | 11/2014 | Grenon et al. |
| 2014/0378878 A1 | 12/2014 | Sharma et al. |
| 2015/0005750 A1 | 1/2015 | Kelleher et al. |
| 2015/0038851 A1 | 2/2015 | Hamrah et al. |
| 2015/0057701 A1 | 2/2015 | Kelleher et al. |
| 2015/0100001 A1 | 4/2015 | Bujak |
| 2015/0148711 A1 | 5/2015 | Bujak et al. |
| 2015/0174425 A1 | 6/2015 | Toyos et al. |
| 2015/0182415 A1 | 7/2015 | Olkowski et al. |
| 2015/0320590 A1 | 11/2015 | Whitehurst et al. |
| 2015/0320594 A1 | 11/2015 | Smith |
| 2016/0120692 A1 | 5/2016 | Chen |
| 2016/0120693 A1 | 5/2016 | Guillon et al. |
| 2016/0243116 A1 | 8/2016 | Jain et al. |
| 2016/0317379 A1 | 11/2016 | Mosaddegh |

(56) References Cited

U.S. PATENT DOCUMENTS

| | | |
|---|---|---|
| 2017/0014300 A1 | 1/2017 | Dippo et al. |
| 2017/0079834 A1 | 3/2017 | Badawi |
| 2017/0079842 A1 | 3/2017 | Maskin |

FOREIGN PATENT DOCUMENTS

| | | |
|---|---|---|
| CA | 2679448 A1 | 9/2008 |
| CA | 2787114 A1 | 7/2011 |
| CA | 2809274 A1 | 3/2012 |
| CN | 1781466 A | 6/2001 |
| CN | 2650737 Y | 10/2004 |
| CN | 1631344 A | 6/2005 |
| CN | 2855388 Y | 1/2007 |
| CN | 1297719 A | 6/2011 |
| CN | 102204854 A | 10/2011 |
| CN | 101663064 B | 3/2013 |
| CN | 103002737 A | 3/2013 |
| CN | 103108669 A | 5/2013 |
| CN | 102600008 B | 5/2014 |
| CN | 103816033 A | 5/2014 |
| CN | 103948490 A | 7/2014 |
| CN | 102697593 B | 12/2014 |
| CN | 102697595 B | 12/2014 |
| CN | 104203190 A | 12/2014 |
| CN | 104398234 A | 3/2015 |
| DE | 202005011496 U1 | 7/2006 |
| EP | 1816980 A2 | 8/2007 |
| EP | 2151438 A1 | 2/2010 |
| EP | 1587468 B1 | 1/2011 |
| EP | 2523556 A1 | 11/2012 |
| JP | H0370557 A | 3/1991 |
| JP | 06269473 A | 9/1994 |
| JP | H06315499 A | 11/1994 |
| JP | 10085248 A | 4/1998 |
| JP | 11221247 | 8/1999 |
| JP | 2000225141 A | 8/2000 |
| JP | 2001276113 A | 10/2001 |
| JP | 2002078727 A | 3/2002 |
| JP | 2004350803 A | 12/2004 |
| JP | U3112008 B | 7/2005 |
| JP | 2005237724 A | 9/2005 |
| JP | 2006198249 A | 8/2006 |
| JP | 2010155012 A | 7/2010 |
| JP | 2014205069 A | 10/2014 |
| KR | 20120115380 A | 10/2012 |
| KR | 101806298 B1 | 12/2017 |
| MX | 2012008110 A | 10/2012 |
| WO | 9810723 A1 | 3/1998 |
| WO | 9920213 A1 | 4/1999 |
| WO | 9958131 A1 | 11/1999 |
| WO | 2004041134 A1 | 5/2004 |
| WO | 2006058189 A2 | 6/2006 |
| WO | 2006093851 A2 | 9/2006 |
| WO | 2008024100 A2 | 2/2008 |
| WO | 2008106228 A2 | 9/2008 |
| WO | 2009064834 A2 | 5/2009 |
| WO | 2010005527 A1 | 1/2010 |
| WO | 2010056848 A1 | 5/2010 |
| WO | 2011085385 A1 | 7/2011 |
| WO | 2012036931 A1 | 3/2012 |
| WO | 2012051313 A2 | 4/2012 |
| WO | 2013003594 A3 | 1/2013 |
| WO | 2013003731 A3 | 1/2013 |
| WO | 2013006574 A1 | 1/2013 |
| WO | 2013036894 A2 | 3/2013 |
| WO | 2013114127 A1 | 8/2013 |
| WO | 2013126599 A1 | 8/2013 |
| WO | 2013149318 A1 | 10/2013 |
| WO | 2013166353 A1 | 11/2013 |
| WO | 2014049841 A1 | 4/2014 |
| WO | 2014158356 A1 | 10/2014 |
| WO | 2014179356 A1 | 11/2014 |
| WO | 2014179795 A2 | 11/2014 |
| WO | 2015163821 A1 | 10/2015 |
| WO | 2016070134 A1 | 5/2016 |
| WO | 2017072575 A1 | 5/2017 |
| WO | 2017100608 A1 | 6/2017 |
| WO | 2017156002 A1 | 9/2017 |
| WO | 2017178892 A3 | 11/2017 |
| WO | 2018004234 A1 | 1/2018 |

OTHER PUBLICATIONS

Non-Final Office Action for U.S. Appl. No. 12/015,593, dated Jun. 4, 2015, 20 pages.
Third Office Action for Chinese Patent Application No. 201210127347.3, dated Jun. 26, 2015, 7 pages.
Examination Report for European Patent Application No. 06801969.4, dated Jul. 6, 2015, 5 pages.
Notice of Allowance for U.S. Appl. No. 13/183,901, dated Aug. 12, 2015, 11 pages.
No Author, "arGentis Licenses Third Treatment for Dry Eye Syndrome", Business Wire, May 12, 2008, accessed Jun. 4, 2008, 2 pages.
No Author, "New Over-the-Counter Dry Eye Drop Now Available to Help Estimated 40 Percent of Americans Who Suffer from Occasional or Chronic Dry Eye", Business Wire News Release, Mar. 31, 2008, accessed Jun. 5, 2008, 4 pages.
Akyol-Salman, Ilknur et al., "Efficacy of Topical N-Acetylcysteine in the Treatment of Meibomian Gland Dysfunction," Journal of Ocular Pharmacology and Therapeutics, vol. 26, No. 4, Aug. 1, 2010, pp. 329-333.
Aronowicz, JD et al. "Short Term Oral Minocycline Treatment of Meibomiantis," Br. J. Ophthalmol, vol. 90, No. 7, Jul. 2006, pp. 856-860.
Blackie, Caroline A. et al., "Inner Eyelid Surface Temperature as a Function of Warm Compress Methodology," Optometry and Vision Science, vol. 85, No. 8, Aug. 2008, pp. 675-683.
Blackie, Caroline A. et al., "Nonobvious Obstructive Meibomian Gland Dysfunction," Cornea, vol. 29, No. 12, Dec. 2010, pp. 1333-1345.
Blackie, Caroline A. et al., "Recovery Time of an Optimally Secreting Meibomian Gland," Cornea, vol. 28, No. 3, Apr. 2009, pp. 293-297.
Butovich, Igor et al., "Meibomian Lipid Films and the Impact of Temperature," Investigative Opthalmology & Visual Science, vol. 51, No. 11, Jul. 2010, pp. 5508-5518.
Cunniffe, M. Geraldine et al., "Topical Antiglaucoma Treatment with Prostaglandin Analogues May Precipitate Meibomian Gland Disease," Ophthalmic Plastic and Reconstructive Surgery, Sep.-Oct. 2011, vol. 27, No. 5, Lippincott Williams and Wilkins, Philadelphia, PA, p. 128-129.
Dausch, Eva et al., "Dry Eye Syndrome in Women's Health and Gynecology: Etiology, Pathogenesis and Current Therapeutic Strategies," Geburtshilfe und Frauenheilkunde, vol. 70, No. 9, Jan. 1, 2010, pp. 707-711. (Abstract Only).
Donnenfeld, Eric et al., "Topical Ophthalmic Cyclosporine: Pharmacology and Clinical Uses," Survey of Ophthalmology, vol. 54, No. 3, May/Jun. 2009, pp. 321-338.
Foulks, Gary N. et al., "Topical Azithromycin Therapy for Meibomian Gland Dysfunction: Clinical Response and Lipid Alterations," Cornea, vol. 29, No. 7, Jul. 2010, pp. 781-788.
Foulks, Gary N. et al., "Meibomian Gland Dysfunction: The Past, Present, and Future," Eye and Contact Lens, vol. 36, No. 5, Sep. 2010, pp. 249-253.
Friedland, B., et al., "A Novel Thermodynamic Treatment for Meibomian Gland Dysfunction," Current Eye Research, vol. 36, No. 2, Feb. 2011, pp. 79-87.
Geerling, G., et al., "The international workshop on meibomian gland dysfunction: report of the subcommittee on management and treatment of meibomian gland dysfunction," Mar. 2011, Investigative Ophthalmology & Visual Science, vol. 52, No. 4., pp. 2050-2064.
Goto, E., et al. "Treatment of Non-Inflamed Obstructive Meibomian Gland Dysfunction by an Infrared Warm Compression Device," Br. J. Ophthalmology, vol. 86, Dec. 2002, pp. 1403-1407.

(56) References Cited

OTHER PUBLICATIONS

Goto, Eiki, et al., "Tear Evaporation Dynamics in Normal Subjects and Subjects with Obstructive Meibomian Gland Dysfunction," Investigative Ophthalmology & Visual Science, vol. 44, No. 2, Feb. 2003, pp. 533-539.
Greiner, J., "A Single LipiFlow Thermal Pulsation System Treatment Improves Meibomian Gland Function and Reduces Dry Eye Symptoms for 9 months," Current Eye Research, vol. 37 No. 4, Apr. 2012, pp. 272-278.
Gupta, S. et al. "Docetaxel-Induced Meibomian Duct Inflammation and Blockage Leading to Chalazion Formation," Prostate Cancer and Prostatic Diseases, vol. 10, No. 4, Apr. 2007, pp. 396-397.
Haque, Reza M. et al., "Multicenter Open-label Study Evaluating the Efficacy of Azithromycin Opthalmic Solution 1% on the Signs and Symptoms of Subjects with Blepharitis," Cornea, vol. 29, No. 8, Aug. 2010, pp. 871-877.
Holifield, Karintha and Lazzaro, Douglas R., "Case report: Spontaneous stenotrophomonas maltophilia keratitis in a diabetic patient," Eye and Contact Lens, Sep. 2011, vol. 37, No. 5, Philadelphia PA, pp. 326-327.
Knop, E. et al., "Meibomian Glands: Part III—Dysfunction—Argument for a Discrete Disease Entity and as an Important Cause of Dry Eye," Ophthalmologe, vol. 106, No. 11, Nov. 2009, pp. 966-979. (Abstract Only).
Knop, E. et al., "Meibomian Glands: Part IV—Functional Interactions in the Pathogenesis of Meibomian Gland Dysfunction (MGD)," Ophthalmologe, vol. 106, No. 11, Nov. 2009, pp. 980-987. (Abstract Only).
Kokke, K.H. et al., "Oral Omega-6 Essential Fatty Acid Treatment in Contact Lens Associated Dry Eye," Contact Lens and Anterior Eye, vol. 31, No. 3, Jun. 2008, pp. 141-146.
Korb, Donald et al., "The Effect of Two Novel Lubricant Eye Drops on Tear Film Lipid Layer Thickness in Subjects with Dry Eye Symptoms," Optom. Vis. Sci., vol. 82, No. 7, 2005, pp. 594-601.
Korb, Donald R. and Blackie, Caroline A., "Meibomian gland therapeutic expression: Quantifying the applied pressure and the limitation of resulting pain," Eye and Contact Lens, Sep. 2011, vol. 37, No. 5, Philadelphia, PA, pp. 298-301.
Korb, Donald R. et al., "Increase in Tear Film Lipid Layer Thickness Following Treatment of Meibomian Gland Dysfunction", Lacrimal Gland, Tear Film & Dry Eye Syndromes, vol. 350, Plenum Press, 1994, pp. 293-298.
Korb, Donald R. et al., "Lid Wiper Epitheliopathy and Dry Eye Symptoms," Eye & Contact Lens, vol. 31, No. 1, Jan. 2005, pp. 2-8.
Korb, Donald R. et al., "Restoration of Meibomian Gland Functionality with Novel Thermodynamic Treatment Device—A Case Report," Cornea, vol. 29, No. 8, Aug. 2010, pp. 930-933.
Korb, Donald R. et al., "Tear Film Lipid Layer Thickness as a Function of Blinking," Cornea, vol. 13, No. 4, Jul. 1994, pp. 354-359.
Korb, Donald R. et al., Slide entitled "Inner Eyelid Surface Temperature as a Function of Warm Compress Methodology," from presentation entitled "The Greatest Anterior Segment Disease and Contact Lens Complications Course," AOA Meeting, Seattle, Washington, Jun. 27, 2008, 2 pages.
Korb, Donald R., O.D., et al., "Meibomian Gland Dysfunction and Contact Lens Intolerance," Journal of the American Optometric Association, vol. 51, No. 3, Mar. 1980, pp. 243-251.
Korb, Donald R., Slide entitled "Inner Eyelid Surface Temperature as a Function of Warm Compress Methodology," from presentation entitled "The Tear Film and Dry Eye States A Fertile Research Area," University of California at Berkeley, School of Optometry, Apr. 11, 2008. 2 pages.
Kuscu, Naci Kemal, et al., "Tear Function Changes of Postmenopausal Women in Response to Hormone Replacement Therapy," Maturitas, vol. 44, Jan. 2003pp. 63-68.
Lane, S. et al., "A New System, the LipiFlow, for the Treatment of Meibomian Gland Dysfunction," Cornea, vol. 31, No. 4, Apr. 2012, pp. 396-404.

Lemp, Michael A. et al., "Blepharitis in the United States 2009: A Survey-Based Perspective on Prevalence and Treatment." Oculular Surface, vol. 7, No. 2 Supplement, Apr. 2009, 36 pages.
Lemp, Michael A., et al., "The Therapeutic Role of Lipids—Managing Ocular Surface Disease," Supplement to Refractive Eyecare of Ophthalmologists, vol. 9, No. 6, Jun. 2005, 14 pages.
Maskin, Steven L., "Intraductal Meibomian Gland Probing Relieves Symptoms of Obstructive Meibomian Gland Dysfunction," Cornea, vol. 29, No. 10, Oct. 2010, pp. 1145-1152.
Matsumoto, Yukihiro et al., "The Evaluation of the Treatment Response in Obstructive Meibomian Gland Disease by In Vivo Laser Confocal Microscopy," Graefes Arch Clin Exp Ophthalmol, vol. 247, No. 6, Jun. 2009, pp. 821-829.
Unknown, "Introducing: Thermofoil Heaters", Minco Bulletin HS-202, 2002, 9 pages.
Mitra, M. et al., "Tear Film Lipid Layer Thickness and Ocular Comfort after Meibomian Therapy via Latent Heat with a Novel Device in Normal Subjects," Eye, Jun. 2005, pp. 657-660.
Mori, A., et al., "Efficacy of the Treatment by the Disposable Eyelid Warming Instrument for Meibomian Gland Dysfunction," Poster Presentation, Hall A, The Association for Research and Vision in Ophthalmology Annual Meeting, Fort Lauderdale, Florida, Apr. 30, 2000, 1 page.
Mori, Asako, et al., "Disposable Eyelid-Warming Device for the Treatment of Meibomian Gland Dysfunction", Japan Journal of Ophthalmology, vol. 47, pp. 578-586, 2003.
Olson, Mary Catherine, B.A., et al., "Increase in Tear Film Lipid Layer Thickness Following Treatment with Warm Compresses in Patients with Meibomian Gland Dysfunction," Eye & Contact Lens, vol. 29, No. 2, Apr. 2003, pp. 96-99.
Paugh, J.R. et al., "Meibomian Therapy in Problematic Contact Lens Wear," Entrez PubMed, Optom Vis Sci, vol. 67, No. 11, Nov. 1990, pp. 803-806 (abstract only).
Paugh, Jerry R. et al., "Precorneal Residence Time of Artificial Tears Measured in Dry Eye Subjects," Optometry and Vision Science, vol. 85, No. 8, Aug. 2008, pp. 725-731.
Romero, Juan M., et al., "Conservative Treatment of Meibomian Gland Dysfunction," Contact Lens Association of Ophthalmology, Eye & Contact Lens, vol. 30, No. 1, Jan. 2004, pp. 14-19.
Sullivan, Benjamin D., et al., "Impact of Antiandrogen Treatment on the Fatty Acid Profile of Neutral Lipids in Human Meibomian Gland Secretions," Journal of Clinical Endocrinology & Metabolism, vol. 85, No. 12, Dec. 2000, pp. 4866-4873.
Sullivan, David et al., "Do Sex Steroids Exert Sex-Specific and/or Opposite Effects on Gene Expression in Lacrimal and Meibomian Glands?" Molecular Vision, vol. 15, No. 166, Aug. 10, 2009, pp. 1553-1572.
Suzuki, Tomo et al., "Estrogen and Progesterone Control of Gene Expression in the Mouse Meibomian Gland," Invest. Ophthalmol. Vis. Sci., vol. 49, No. 5, May 2008, pp. 1797-1818.
Final Office Action for U.S. Appl. No. 11/541,308, dated Oct. 25, 2017, 25 pages.
Notice of Allowance for U.S. Appl. No. 14/074,123, dated Oct. 25, 2017, 8 pages.
Final Office Action for U.S. Appl. No. 14/746,328, dated Nov. 16, 2017, 12 pages.
Second Examination Report for Indian Patent Application No. 1318/MUMNP/2009, dated Nov. 18, 2017, 2 pages.
Non-Final Office Action for U.S. Appl. No. 11/541,308, dated Apr. 27, 2017, 21 pages.
First Examination Report for Indian Patent Application No. 1318/MUMNP/2009, dated Mar. 14, 2017, 20 pages.
Author Unknown, "Home," http://www.heatedeyepad.com/home.html, accessed Dec. 16, 2016, Digital Heat, 2 pages.
Author Unknown, "Product," http://www.heatedeyepad.com/product.html, accessed Dec. 16, 2016, Digital Heat, 2 pages.
Non-Final Office Action for U.S. Appl. No. 14/074,123, dated Dec. 29, 2016, 23 pages.
Author Unknown, "Appendages of the eye," The Free Dictionary by Farlex, Medical Dictionary, retrieved on Feb. 8, 2016, medical-dictionary.thefreedictionary.com/appendages+of+the+eye, Farlex and Partners, 1 page.

(56) References Cited

OTHER PUBLICATIONS

Author Unknown, "Medical Definition of Orbit," Merriam-Webster Dictionary, retrieved Feb. 8, 2016, www.merriam-webster.com/medical/orbit, Merriam-Webster, Incorporated, 2 pages.

Goslin, Krysta, et al., "Evaluation of a Single Thermal Pulsation Treatment for Dry Eye and Meibomian Gland Dysfunction and Likelihood of Positive SJO Test," Investigative Ophthalmology & Visual Science, vol. 56, Jun. 2015, The Association for Research in Vision and Ophthalmology, 2 pages (Meeting Abstract).

Hynes, Michael, et al., "Design of a subtarsal ultrasonic transducer for mild hyperthermia of meibomian glands treating Dry Eye Disease," Investigative Ophthalmology & Visual Science, vol. 56, Jun. 2015, The Association for Research in Vision and Ophthalmology, 3 pages (Meeting Abstract).

Nakayama, Naohiko, et al., "Analysis of Meibum Before and After Intraductal Meibomian Gland Probing in Eyes with Obstructive Meibomian Gland Dysfunction," Cornea, vol. 34, Issue 10, Oct. 2015, Wolters Kluwer Health, Inc., pp. 1206-1208.

Nakayama, Naohiko, et al., "Analysis of Meibum Before and Following Intraductal Meibomian Gland Probing for Eyes with Obstructive Meibomian Gland Dysfunction," Investigative Ophthalmology & Visual Science, vol. 56, Jun. 2015, The Association for Research in Vision and Ophthalmology, 2 pages (Meeting Abstract).

Ngo, William, et al., "Effect of Lid Debridement-Scaling on Dry Eye Signs and Symptoms in Sjogren's Syndrome," Investigative Ophthalmology & Visual Science, vol. 56, Jun. 2015, The Association for Research in Vision and Ophthalmology, 2 pages (Meeting Abstract).

Tanabe, Hirotaka, et al., "Effect of Eye Shampoo for Obstructive Meibomian Gland Disease," Investigative Ophthalmology & Visual Science, vol. 56, Jun. 2015, The Association for Research in Vision and Ophthalmology, 2 pages (Meeting Abstract).

Vegunta, Srav, et al., "Tear osmolarity measurements in ocular graft-versus-host disease patients undergoing intense pulsed light (IPL) and meibomian gland expression (MGX)," Investigative Ophthalmology & Visual Science, vol. 56, Jun. 2015, The Association for Research in Vision and Ophthalmology, 2 pages (Meeting Abstract).

Final Office Action for U.S. Appl. No. 12/015,593, dated Feb. 16, 2016, 22 pages.

Non-Final Office Action for U.S. Appl. No. 14/510,843, dated Feb. 4, 2016, 10 pages.

Notice of Allowance for U.S. Appl. No. 12/015,600, dated Jan. 20, 2016, 7 pages.

Non-Final Office Action for U.S. Appl. No. 13/590,828, dated Feb. 26, 2016, 11 pages.

Non-final Office Action for U.S. Appl. No. 13/368,976 dated Aug. 31, 2012, 10 pages.

Non-final Office Action for U.S. Appl. No. 11/541,308 dated Aug. 31, 2012, 20 pages.

Non-final Office Action for U.S. Appl. No. 13/242,068 dated Aug. 29, 2012, 9 pages.

Non-final Office Action for U.S. Appl. No. 13/367,908 dated Sep. 13, 2012, 11 pages.

Willis, et al., Meibomian gland function, lid wiper epitheliopathy, and dry eye symptoms, ARVO Annual Meeting, May 2011, pp. 3740 (Abstact only).

Asbell, P. et al. "The international workshop on meibomian gland dysfunction: report of the clinical trials subcommittee," Investigative Ophthalmology and Visual Science, Mar. 2011, pp. 2065-2085.

Office Action for Japanese patent application 2009-546506 dated Sep. 4, 2012, 6 pages.

Foulks et al., "Improving awareness, identification, and management of meibomian gland dysfunction," Ophthalmology, vol. 119, No. 10 Sup., Oct. 2012, 12 pages.

Arita, F. et al., "Comparison of the long-term effects of various topical antiglaucoma medications on meibomian glands," Cornea, vol. 31, No. 11, Nov. 2012, pp. 1229-1234.

Non-final Office Action for U.S. Appl. No. 11/931,398 dated Nov. 2, 2012, 8 pages.

Agnifili et al., "In vivo confocal microscopy of meibomian glands in glaucoma," British Journal of Ophthalmology, vol. 97, No. 3, Mar. 2013, pp. 343-349, United Kingdom.

Aragona, P. et al., "Towards a dynamic customised therapy for ocular surface dysfunctions," British Journal of Ophthalmology, vol. 97, No. 8, Aug. 13, pp. 955-960.

Arita, R. et al., "Topical diquafosol for patients with obstructive meibomian gland dysfunction," British Journal of Ophthalmology, vol. 97, No. 6, Jun. 2013, pp. 725-729.

Author Unknown, Definition of Platform, Merriam-Webster Dictionary, accessed Dec. 10, 2012, 3 pages, http://www.merriam-webster.com/dictionary/platform.

Author Unknown, Definition of On, Merriam-Webster Dictionary, accessed Dec. 14, 2012, 5 pages, http://www.merriam-webster.com/dictionary/on.

Author Unknown, Definition of Platform, Macmillan Dictionary, accessed Dec. 10, 2012, 2 pages, http://www.macmillandictionary.com/dictionary/british/platform.

Author Unknown, "New Breakthrough Treatment for Evaporative Dry Eye Disease Introduced by Dry Eye Specialist, Mark R. Mandel, M.D.," PR Newswire, Dec. 11, 2012, 2 pages, Hayward, California.

Cuevas, Miguel et al., "Correlations Among Symptoms, Signs, and Clinical Tests in Evaporative-Type Dry Eye Disease Caused by Meibomian Gland Dysfunction (MGD)," Current Eye Research, vol. 37, No. 10, Oct. 2012, pp. 855-863.

Greiner, J., "Long-term 12-month improvement in meibomian gland function and reduced dry eye symptoms with a single thermal pulsation treatment," Clinical and Experimental Ophthalmology, vol. 41, No. 6, Aug. 2013, pp. 524-530.

Her, Y. et al., "Dry eye and tear film functions in patients with psoriasis," Japanese Journal of Ophthalmology, vol. 57, No. 4, Jul. 2013, pp. 341-346.

Khandelwal, et al., "Androgen regulation of gene expression in human meibomian gland and conjunctival epithelial cells," Molecular Vision, vol. 18, Apr. 27, 2012, pp. 1055-1067.

Zhang et al., "Efficacy of physical therapy meibomian gland dysfunction," International Eye Science, International Journal of Ophthalmology, vol. 13, No. 6, Jun. 2013, pp. 1267-1268.

Li, Li-Hu et al., "Analysis of the efficacy in the treatment of meibomian gland dysfunction," International Eye Science, vol. 13, No. 7, Jul. 2013, pp. 1495-1497.

Lin, Hui et al., "Dry eye disease: A review of diagnostic approaches and treatments," Saudi Journal of Ophthalmology, vol. 28, Issue 3, Jul.-Sep. 2014, Saudi Ophthalmological Society, pp. 173-181.

Liu, Ze-Yuan et al., "Treatment of dry eye caused by meibomian gland dysfunction," International Eye Science, vol. 14, No. 2, Feb. 2014, pp. 270-272.

Lu, Hui et al., "Tear film measurement by optical reflectometry technique," Journal of Biomedical Optics, vol. 19, No. 2, Feb. 2014, 8 pages.

Ozer, P.A. et al., "Eyelid nodule in a child: a chalazion or idiopathic facial aseptic granuloma?" Eye, vol. 28, No. 9, Sep. 2014, The Royal College of Ophthalmologists, pp. 1146-1147.

Pucker, A. et al., "Analysis of Meibum and Tear Lipids," The Ocular Surface, vol. 10, No. 4, Oct. 2012, pp. 230-250.

Purslow, Christine, "Evaluation of the ocular tolerance of a novel eyelid-warming device used for meibomian gland dysfunction," Contact Lens & Anterior Eye, vol. 36, No. 5, Elsevier Ltd., Oct. 2013, pp. 226-231.

Suzuki, Tomo, "Meibomitis-Related Keratoconjunctivitis: Implications and Clinical Significance of Meibomian Gland Inflammation," Cornea, vol. 31, Supplemental Issue, Nov. 2012, pp. S41-S44.

Tang, Qin et al., "Clinical analysis of meibomian gland dysfunction in elderly patients," International Eye Science, vol. 13, No. 7, Jul. 2013, pp. 1419-1423.

Non-Final Rejection dated Dec. 27, 2012, for U.S. Appl. No. 12/015,593, 27 pages.

Final Office Action for U.S. Appl. No. 12/015,593 dated Oct. 3, 2013, 21 pages.

(56) References Cited

OTHER PUBLICATIONS

Non-final Office Action for U.S. Appl. No. 11/434,033 dated Feb. 19, 2014, 10 pages.
Final Office Action for U.S. Appl. No. 11/434,033 dated Jun. 2, 2014, 11 pages.
Notice of Allowance for U.S. Appl. No. 11/434,033 dated Aug. 8, 2014, 8 pages.
Final Office Action for U.S. Appl. No. 11/931,398 dated Mar. 4, 2013, 7 pages.
Advisory Action for U.S. Appl. No. 11/931,398 dated May 15, 2013, 2 pages.
Non-final Office Action for U.S. Appl. No. 11/931,398 dated Jun. 3, 2014, 8 pages.
Final Office Action for U.S. Appl. No. 11/541,308 dated Mar. 19, 2013, 25 pages.
Advisory Action for U.S. Appl. No. 11/541,308 dated Jun. 26, 2013, 3 pages.
Non-Final Rejection for U.S. Appl. No. 11/928,681, dated Nov. 20, 2012, 9 pages.
Non-final Office Action for U.S. Appl. No. 11/928,681 dated Nov. 20, 2012, 10 pages.
Final Office Action for U.S. Appl. No. 11/928,681 dated Feb. 26, 2013, 7 pages.
Advisory Action for U.S. Appl. No. 11/928,681 dated May 3, 2013, 3 pages.
Non-final Office Action for U.S. Appl. No. 11/928,681 dated Jun. 4, 2014, 7 pages.
Notice of Allowance for U.S. Appl. No. 11/928,681, dated Sep. 22, 2014, 9 pages.
Non-final Office Action for U.S. Appl. No. 11/931,914 dated Jun. 10, 2014, 15 pages.
First Office Action for Chinese patent application 201210127347.3 dated Jan. 15, 2014, 13 pages.
Second Office Action for Chinese patent application 201210077192.7 dated May 5, 2014, 3 pages.
Non-Final Office Action for U.S. Appl. No. 14/746,328, dated May 31, 2017, 11 pages.
Non-Final Office Action for U.S. Appl. No. 14/618,392, dated Jun. 28, 2017, 23 pages.
Final Office Action for U.S. Appl. No. 14/074,123, dated Jun. 8, 2017, 26 pages.
Advisory Action for U.S. Appl. No. 13/590,828, dated Jan. 27, 2017, 3 pages.
Notice of Allowance for U.S. Appl. No. 13/590,828, dated Mar. 8, 2017, 9 pages.
Fourth Office Action for Chinese Patent Application No. 201210127347.3, dated Feb. 29, 2016, 9 pages.
Decision of Rejection for Japanese Patent Application No. 2013-226709, dated Feb. 2, 2016, 8 pages.
Blackie, Caroline A., et al., "Treatment for meibomian gland dysfunction and dry eye symptoms with a single-dose vectored thermal pulsation: a review," Current Opinion in Ophthamology, vol. 26, Issue 4, Jul. 2015, Lippincott Williams & Wilkins, pp. 306-313.
Doan, S., et al., "Evaluation of an eyelid warming device (Blephasteam®) for the management of ocular surface diseases in France: The ESPOIR study," Journal Français d'Ophtalmologie, vol. 37, Issue 10, Oct. 1, 2014, Elsevier Masson SAS, pp. 763-772.
Thode, Adam R., et al., "Current and Emerging Therapeutic Strategies for the Treatment of Meibomian Gland Dysfunction (MGD)," Drugs, vol. 75, Issue 11, Jul. 1, 2015, Springer International Publishing, pp. 1177-1185.
Vora, Gargi K., et al., "Intense pulsed light therapy for the treatment of evaporative dry eye disease," Current Opinion in Ophthalmology, vol. 26, Issue 4, Jul. 2015, Wolters Kluwer Health, Inc., pp. 314-318.
Advisory Action for U.S. Appl. No. 12/015,600 dated Nov. 3, 2015, 3 pages.
Examination Report for European Patent Application No. 08727830.5 dated Oct. 5, 2015, 5 pages.

Bron, Anthony J. et al., "Rethinking Dry Eye Disease: A Perspective on Clinical Implications," The Ocular Surface, vol. 12, No. 2S, Apr. 2014, Elsevier Inc., 31 pages.
Second Office Action for Chinese Patent Application No. 201210127347.3, dated Nov. 2, 2014, 7 pages.
Notice of Allowance for U.S. Appl. No. 29/303,317 dated Feb. 1, 2010, 8 pages.
Non-final Office Action for U.S. Appl. No. 29/303,317 dated Sep. 1, 2009, 10 pages.
Notice of Allowance for U.S. Appl. No. 12/015,567 dated May 20, 2011, 8 pages.
Non-final Office Action for U.S. Appl. No. 12/015,567 dated Aug. 16, 2010, 9 pages.
Non-final Office Action for U.S. Appl. No. 12/015,576 dated Jul. 19, 2010, 11 pages.
Notice of Allowance for U.S. Appl. No. 12/015,584 dated Jul. 8, 2011, 4 pages.
Notice of Allowance for U.S. Appl. No. 12/015,584 dated Jun. 29, 2011, 7 pages.
Final Office Action for U.S. Appl. No. 12/015,584 dated May 27, 2011, 7 pages.
Non-final Office Action for U.S. Appl. No. 12/015,584 dated Aug. 23, 2010, 9 pages.
Non-final Office Action for U.S. Appl. No. 12/015,600 dated Mar. 19, 2012, 6 pages.
Notice of Allowance for U.S. Appl. No. 12/015,675 dated Oct. 26, 2011, 9 pages.
Non-final Office Action for U.S. Appl. No. 12/015,675 dated May 10, 2011, 7 pages.
Notice of Allowance for U.S. Appl. No. 12/015,683 dated Oct. 26, 2011, 8 pages.
Non-final Office Action for U.S. Appl. No. 12/015,683 dated May 6, 2011, 14 pages.
Notice of Allowance for U.S. Appl. No. 12/015,721 dated Nov. 30, 2011, 8 pages.
Advisory Action for U.S. Appl. No. 12/015,721 dated Aug. 31, 2011, 3 pages.
Final Office Action for U.S. Appl. No. 12/015,721 dated Jun. 8, 2011, 12 pages.
Non-final Office Action for U.S. Appl. No. 12/015,721 dated Jan. 5, 2011, 12 pages.
Notice of Allowance for U.S. Appl. No. 29/344,914 dated Mar. 7, 2011, 8 pages.
Notice of Allowance for U.S. Appl. No. 29/344,914 dated Jan. 12, 2011, 7 pages.
English translation of Japanese Office Action for patent application 2009-525536 dated Jan. 10, 2012, 6 pages.
International Search Report for PCT/US07/00493 dated Oct. 1, 2007, 1 page.
English translation of First Office Action for Chinese patent application 200780039253.8 dated Jul. 12, 2010, 6 pages.
Extended European Search Report for PCT/US2007/000525 dated Sep. 20, 2010, 9 pages.
English translation of Japanese Office Action for patent application 2009-544825 dated Jan. 10, 2012, 9 pages.
International Search Report for PCT/US07/00525 dated Dec. 3, 2007, 12 pages.
Extended European Search Report for patent application 07716445.7-1269 dated Apr. 7, 2011, 9 pages.
English translation of Japanese Office Action for patent application 2009-525537 dated Jan. 10, 2012, 4 pages.
International Search Report for PCT/US07/00508 dated Nov. 2, 2007, 1 page.
English translation of Second Chinese Office Action for patent application 200880008741.7 dated Mar. 29, 2012, 7 pages.
English translation of First Chinese Office Action for patent application 200880008741.7 dated Jul. 20, 2011, 7 pages.
Office Action for Israeli patent application 199920 dated May 22, 2011, 2 pages.
International Search Report for PCT/US08/51309 dated May 20, 2008, 1 page.
English translation of First Office Action for Chinese patent application 200680056181.3 dated Jun. 12, 2010, 6 pages.

(56) References Cited

OTHER PUBLICATIONS

International Search Report for PCT/US06/32544 dated May 12, 2008, 8 pages.
Notice of Allowance for U.S. Appl. No. 12/015,576 dated May 20, 2011, 8 pages.
Final Office Action for U.S. Appl. No. 11/434,033 dated Mar. 15, 2012, 9 pages.
Finis, D. et al., "Meibom-Drusen-Dysfunktion," Klinische Monatsblatter fur Augenheilkunde, vol. 229, No. 5, Mar. 2012, pp. 506-513 (Abstract translated only).
Non-final Office Action for U.S. Appl. No. 13/183,901 dated Jun. 4, 2012, 46 pages.
Korb, et al., "Forceful Meibomian Gland Expression with a Standardized Force of 8 PSI in Patients with Obstructive Meibomian Gland Dysfunction," ARVO Annual Meeting, Poster Session, Program No. 3819, Poster Board No. D952, May 3, 2011, 2 pages (Abstract Only).
Korb, et al., "Prevalence of lid wiper epitheliopathy in subjects with dry eye signs and symptoms," Cornea, vol. 29, No. 4, Apr. 2012, pp. 377-383.
Willis, et al., "Meibomian gland function, lid wiper epitheliopathy, and dry eye symptoms," ARVO Annual Meeting, May 2011, pp. 3740 (Abstract only).
Second Office Action for Japanese patent application 2009-525529 dated Jun. 5, 2012, 8 pages.
Extended European Search Report for patent application 07716441.6 dated Sep. 4, 2012, 7 pages.
Foulks, G. et al., Comparative Effectiveness of Azithromycin and Doxycycline in Therapy of Meibomian Gland Dysfunction, ARVO Annual Meeting, May 2011, pp. 3816 (Abstract only).
Korb, et al., "Restoration of meibomian gland function post Lipiflow treatment," ARVO Annual Meeting, May 2011, pp. 3818 (Abstract only).
Maskin, S. et al., "Intraductal Meibomian Gland Probing with Adjunctive Intraductal Microtube Steriod Injection (MGPs) for Meibomian Gland Dysfuction," ARVO Annual Meeting, May 2011, pp. 3817 (Abstract only).
McCann, L. et al., "Effect of First Line Management Therapies on Dry Eye Disease," ARVO Annual Meeting, May 2011, pp. 3829 (Abstract only).
Yoshitomi, et al., "Meibomian Gland Compressor and Cataract Surgery," New Ophthalmology, Japan, 2001, vol. 18, No. 3, pp. 321-323 (Need English Abstract/Translation).
Tobler, David, et al., "Nanotech Silver Fights Microbes in Medical Devices," Medical Device and Diagnostic Industry, May 1, 2005, p. 164.
Toyos, Rolando, "Intense Pulsed Light for Dry Eye Syndrome," Cataract & Refractive Surgery Today, Apr. 2009, pp. 1-3.
Wolff, Eugene, "Eugene Wolff's Anatomy of the eye and orbit : including the central connexions, development, and comparative anatomy of the visual apparatus (book)," 1976, p. 170.
Unknown, "IFU Manual for PNT Model 1000—Rev H," Feb. 11, 2009, http://www.oi-pnt.com/files/IFU_Manual_Model_1000_English_with_Bargode_Rev_H.pdf, 24 pages.
Unknown, "TearScience Launches Breakthrough Technology in Canada to Address the Root Cause of Evaporative Dry Eye," Business Wire, Jun. 9, 2011, http://www.businesswire.com/news/home/20110609005860/en/TearScience-Launches-Breakthrough-Technology-Canada-Address-Root, 2 pages.
Vasta, Stephanie, "Aggressive Treatments Developed for Meibomian Gland Dysfunction," Primary Care Optometry News, Nov. 1, 2009, 3 pages.
Wang, Y. et al., "Baseline Profiles of Ocular Surface and Tear Dynamics After Allogeneic Hematopoietic Stem Cell Transplantation in Patients With or Without Chronic GVHD-Related Dry Eye," Bone Marrow Transplantation, vol. 45, No. 6, Jun. 2010, pp. 1077-1083.
Korb, D. et al., "Meibomian gland therapeutic expression: quantifying the applied pressure and the limitation of resulting pain," Eye & Contact Lens, vol. 37 No. 5, Sep. 2011, pp. 298-301.
Akyol-Salman, I. et al., "Comparison of the efficacy of topical N-acetyl-cysteine and a topical steroid-antibiotic combination therapy in the treatment of meibomian gland dysfunction," Journal of Ocular Pharmacology and Therapeutics, vol. 28 No. 1, Feb. 2, 2012, pp. 49-52.
No Author, "TearScience's LipiFlow Multi-center Clinical Study Shows Improved Meibomian Gland Secretions and Dry Eye Symptoms," Business Wire, Mar. 5, 2012, 2 pages.
Non-Final Rejection for U.S. Appl. No. 11/434,033 dated Jan. 24, 2011, 7 pages.
Non-final Office Action for U.S. Appl. No. 11/434,033 dated Aug. 12, 2011, 8 pages.
Non-final Office Action for U.S. Appl. No. 11/931,398 dated Jan. 27, 2012, 4 pages.
Advisory Action for U.S. Appl. No. 11/434,446 dated Mar. 4, 2010, 2 pages.
Final Rejection for U.S. Appl. No. 11/434,446 dated Dec. 23, 2009, 16 pages.
Non-final Rejection for U.S. Appl. No. 11/434,446 dated Apr. 9, 2010, 17 pages.
Non-Final Rejection for U.S. Appl. No. 11/434,446 dated Jun. 17, 2009, 13 pages.
English translation of Official Action dated May 10, 2011, for Japanese Patent Application No. 2009-525529, 3 pages.
Notice of Allowance for U.S. Appl. No. 13/025,951 dated Mar. 28, 2012, 8 pages.
Non-final Office Action for U.S. Appl. No. 13/025,951 dated Oct. 25, 2011, 9 pages.
Notice of Allowance for U.S. Appl. No. 13/025,990 dated Mar. 28, 2012, 9 pages.
Non-final Office Action for U.S. Appl. No. 13/025,990 dated Oct. 25, 2011, 11 pages.
Notice of Allowance for U.S. Appl. No. 11/434,054 dated Oct. 18, 2011, 9 pages.
Non-final Office Action for U.S. Appl. No. 11/434,054 dated May 26, 2011, 7 pages.
Non-final Office Action for U.S. Appl. No. 11/434,054 dated Sep. 8, 2010, 7 pages.
Non-final Office Action for U.S. Appl. No. 11/434,054 dated Mar. 12, 2010, 7 pages.
Notice of Allowance for U.S. Appl. No. 12/821,183 dated Jul. 29, 2011, 8 pages.
Non-final Office Action for U.S. Appl. No. 12/821,183 dated May 26, 2011, 8 pages.
Non-final Office Action for U.S. Appl. No. 12/821,183 dated Dec. 21, 2010, 7 pages.
Notice of Allowance for U.S. Appl. No. 11/541,291 dated May 26, 2011, 7 pages.
Notice of Allowance for U.S. Appl. No. 11/541,291 dated Jan. 10, 2011, 6 pages.
Final Office Action for U.S. Appl. No. 11/541,291 dated Aug. 17, 2010, 6 pages.
Non-final Office Action for U.S. Appl. No. 11/541,291 dated Jun. 2, 2010, 10 pages.
Advisory Action for U.S. Appl. No. 11/541,291 dated Mar. 30, 2010, 3 pages.
Final Office Action for U.S. Appl. No. 11/541,291 dated Dec. 16, 2009, 11 pages.
Non-final Office Action for U.S. Appl. No. 11/541,291 dated May 19, 2009, 11 pages.
Notice of Allowance for U.S. Appl. No. 11/931,646 dated Aug. 5, 2010, 6 pages.
Advisory Action for U.S. Appl. No. 11/931,646 dated Mar. 30, 2010, 3 pages.
Final Office Action for U.S. Appl. No. 11/931,646 dated Dec. 15, 2009, 11 pages.
Non-final Office Action for U.S. Appl. No. 11/931,646 dated May 19, 2009, 11 pages.
Notice of Allowance for U.S. Appl. No. 11/541,418 dated May 26, 2011, 7 pages.
Advisory Action for U.S. Appl. No. 11/541,418 dated Apr. 6, 2011, 3 pages.

(56) References Cited

OTHER PUBLICATIONS

Final Office Action for U.S. Appl. No. 11/541,418 dated Mar. 10, 2011, 21 pages.
Non-final Office Action for U.S. Appl. No. 11/541,418 dated Jul. 12, 2010, 20 pages.
Notice of Allowance for U.S. Appl. No. 12/015,558 dated Jun. 1, 2011, 8 pages.
Non-final Office Action for U.S. Appl. No. 12/015,558 dated Aug. 13, 2010, 9 pages.
Non-final Office Action for U.S. Appl. No. 11/928,681 dated Feb. 2, 2012, 4 pages.
Notice of Allowance for U.S. Appl. No. 29/303,312 dated Mar. 1, 2010, 7 pages.
Notice of Allowance for U.S. Appl. No. 29/303,314 dated Feb. 5, 2010, 6 pages.
Final Office Action for U.S. Appl. No. 29/303,314 dated Dec. 28, 2009, 6 pages.
Author Unknown, "Simple Definition of Around," Merriam-Webster's Learner's Dictionary, accessed Aug. 15, 2016, www.merriam-webster.com/dictionary/around, 1 page.
Author Unknown, Definition of "Orbit," Miller-Keane Encyclopedia and Dictionary of Medicine, Nursing, and Allied Health, Seventh Edition, 2003, Saunders, medical-dictionary.thefreedictionary.com/orbit, accessed Sep. 29, 2016, 1 page.
Author Unknown, "Medical Definition of Periorbital," Merriam-Webster: Medical Dictionary, accessed Aug. 15, 2016, www.merriam-webster.com/medical/periorbital, 1 page.
Di Pascuale, Mario A., et al, "Lipid tear deficiency in persistent dry eye after laser in situ keratomileusis and treatment results of new eye-warming device," Journal of Cataract & Refractive Surgery, vol. 31, Issue 9, Sep. 2005, Elsevier, pp. 1741-1749.
Hynes, Michael, B., et al., "Design of a Subtarsal Ultrasonic Transducer for Mild Hyperthermia Treatment of Dry Eye Disease," Ultrasound in Medicine & Biology, vol. 42, Issue 1, Jan. 2016, Elsevier Inc., pp. 232-242.
Matsumoto, Yukihiro, et al., "Efficacy of a New Warm Moist Air Device on Tear Functions of Patients With Simple Meibomian Gland Dysfunction," Cornea, vol. 25, Issue 6, Jul. 2006, Lippincott Williams & Wilkins, pp. 644-650.
Non-Final Office Action for U.S. Appl. No. 11/541,308, dated Sep. 29, 2016, 26 pages.
Non-Final Office Action for U.S. Appl. No. 14/618,392, dated Sep. 30, 2016, 11 pages.
Final Office Action for U.S. Appl. No. 14/510,843, dated Aug. 25, 2016, 13 pages.
Final Office Action for U.S. Appl. No. 13/590,828, dated Sep. 9, 2016, 12 pages.
Extended European Search Report for European Patent Application No. 16170742.7, dated Sep. 8, 2016, 8 pages.
Notice of Rejection for Japanese Patent Application No. 2013-226709, dated Mar. 24, 2015, 10 pages.
Final Office Action for U.S. Appl. No. 12/015,600 dated May 21, 2015, 12 pages.
Advisory Action for U.S. Appl. No. 12/015,593 dated Dec. 13, 2013, 3 pages.
Non-final Office Action for U.S. Appl. No. 12/015,593 dated Mar. 14, 2014, 19 pages.
Final Office Action for U.S. Appl. No. 12/015,593 dated Jul. 7, 2014, 19 pages.
Advisory Action for U.S. Appl. No. 12/015,593, dated Oct. 16, 2014, 3 pages.
Non-Final Rejection dated Jan. 4, 2013, for U.S. Appl. No. 12/015,600, 8 pages.
Non-final Office Action for U.S. Appl. No. 12/015,600 dated Aug. 5, 2013, 8 pages.
Final Office Action for U.S. Appl. No. 12/015,600 dated Apr. 29, 2014, 9 pages.
Advisory Action for U.S. Appl. No. 12/015,600 dated Jul. 16, 2014, 3 pages.

Non-final Office Action for U.S. Appl. No. 12/887,165 dated Apr. 10, 2013, 13 pages.
Notice of Allowance for U.S. Appl. No. 12/887,165 dated Sep. 3, 2013, 10 pages.
Final Rejection dated Dec. 27, 2012, for U.S. Appl. No. 13/183,901, 10 pages.
Advisory Action for U.S. Appl. No. 13/183,901 dated Mar. 11, 2013, 3 pages.
Non-final Office Action for U.S. Appl. No. 13/183,901 dated Oct. 4, 2013, 10 pages.
Final Office Action for U.S. Appl. No. 13/183,901 dated Feb. 3, 2014, 10 pages.
Advisory Action and Applicant-Initiated Interview Summary for U.S. Appl. No. 13/183,901 dated Apr. 21, 2014, 5 pages.
Final Office Action for U.S. Appl. No. 13/368,976 dated Mar. 11, 2013, 8 pages.
Advisory Action for U.S. Appl. No. 13/368,976 dated Jul. 10, 2013, 3 pages.
Notice of Allowance for U.S. Appl. No. 13/368,976 dated Aug. 30, 2013, 9 pages.
Final Rejection for U.S. Appl. No. 13/242,068, dated Feb. 14, 2013, 10 pages.
Final Office Action for U.S. Appl. No. 13/242,068 dated Feb. 14, 2013, 10 pages.
Non-final Office Action for U.S. Appl. No. 13/242,068 dated Jul. 3, 2013, 7 pages.
Notice of Allowance for U.S. Appl. No. 13/242,068 dated Nov. 12, 2013, 10 pages.
Final Office Action for U.S. Appl. No. 13/367,865 dated Mar. 4, 2013, 7 pages.
Notice of Allowance for U.S. Appl. No. 13/367,865 dated May 23, 2013, 9 pages.
Final Office Action for U.S. Appl. No. 13/367,908 dated Feb. 27, 2013, 7 pages.
Advisory Action for U.S. Appl. No. 13/367,908 dated May 22, 2013, 3 pages.
Notice of Allowance for U.S. Appl. No. 13/367,908 dated Aug. 19, 2013, 8 pages.
European Search Report for patent application 06801969.4 dated Nov. 5, 2012, 4 pages.
Examination Report for Indian patent application 563/MUMNP/2009 dated Oct. 31, 2012, 1 pages.
Examination Report dated Oct. 17, 2012, for European Application No. 07716444.0, 5 pages.
Examination Report dated Nov. 16, 2012, for European Application No. 06801969.4, 6 pages.
Examination Report for European Patent Application No. 07716441.6 dated May 19, 2014, 4 pages.
International Search Report dated Jan. 7, 2013, for PCT/US12/44650, 44 pages.
International Preliminary Report on Patentability for PCT/US2012/044650 dated Jan. 16, 2014, 41 pages.
Examination Report for Indian Patent Application No. 564/MUMNP/2009, dated Jan. 30, 2013, 1 page.
Examination Report for Indian Patent Application No. 555/MUMNP/2009, dated Apr. 15, 2013, 1 page.
European Search Report for European Patent Application No. 08727830.5 dated Dec. 20, 2012, 3 pages.
Examination Report for European Patent Application No. 08727830.5 dated Jan. 15, 2013, 5 pages.
Examiner's Decision of Rejection for Japanese Patent Application No. 2009-525537 dated Jan. 7, 2014, 6 pages.
First Office Action for Chinese patent application 201310017764.7 dated Mar. 31, 2014, 20 pages.
First Office Action for Chinese patent application 201310017761.3 dated May 6, 2014, 12 pages.
Second Office Action for Chinese patent application 201210077169.8 dated May 20, 2014, 3 pages (no translation).
Translation of Notice of Rejection for Japanese Patent Application No. 2009-525529 dated May 14, 2013, 5 pages.

(56) References Cited

OTHER PUBLICATIONS

English translation of Final Japanese Office Action for patent application 2009-544825 dated Jan. 29, 2013, 4 pages.
Examiner's Decision of Rejection for Japanese Patent Application No. 2009-544825 dated Jan. 7, 2014, 6 pages.
English translation of Final Japanese Office Action for patent application 2009-525537 dated Jan. 29, 2013, 4 pages.
First Office Action for Chinese patent application 201210077169.8 dated Nov. 26, 2013, 18 pages.
First Office Action for Chinese patent application 201210077192.7 dated Nov. 22, 2013, 12 pages.
Non-Final Office Action for U.S. Appl. No. 12/015,600 dated Oct. 31, 2014, 9 pages.
Foulks, Gary N. "The Correlation Between the Tear Film Lipid Layer and Dry Eye Disease," Survey of Ophthalmology, vol. 52, Issue 4, Jul.-Aug. 2007, Elsevier Inc., pp. 369-374.
Second Office Action for Chinese Patent Application No. 201310017764.7, dated Nov. 15, 2014, 12 pages.
Zhang, J. et al., "A Meibomian Gland Massage Mechanism for Upper and Lower Eyelids Based on Anti-phase Rolling and Enveloping Movement," Chinese Journal of Medical Instrumentation, vol. 38, No. 4, Jul. 2014, pp. 255-258, 273.
Notice of Allowance for U.S. Appl. No. 11/931,398, dated Jan. 16, 2015, 8 pages.
Non-Final Office Action for U.S. Appl. No. 13/183,901, dated Feb. 12, 2015, 9 pages.
Baumann, A. et al., "Meibomian gland dysfunction: A comparative study of modern treatments," French Journal of Ophthalmology, vol. 37, No. 4, Apr. 2014, Elsevier Masson SAS, pp. 303-312.
Dudee, Jitander S., "Affidavit," dated Aug. 26, 2016, 2 pages.
U.S. Appl. No. 09/178,772, filed Oct. 26, 1998, not published.
Advisory Action for U.S. Appl. No. 14/746,328, dated Mar. 5, 2018, 3 pages.
Non-Final Office Action for U.S. Appl. No. 14/618,392, dated Mar. 15, 2018, 17 pages.
Non-Final Office Action for U.S. Appl. No. 11/541,308, dated Mar. 21, 2018, 21 pages.
Non-Final Office Action for U.S. Appl. No. 14/746,328, dated Apr. 5, 2018, 21 pages.
Final Office Action for U.S. Appl. No. 11/541,308, dated Jul. 26, 2018, 22 pages.
Examination Report for European Patent Application No. 16170742.7, dated Dec. 7, 2018, 6 pages.
Written Opinion for Brazilian Patent Application No. 0806635-3, dated Dec. 18, 2018, 11 pages.
Extended European Search Report for European Patent Application No. 18192086.9, dated Nov. 23, 2018, 8 pages.
Final Office Action for U.S. Appl. No. 14/746,328, dated Jan. 2, 2019, 20 pages.
First Office Action for Chinese Patent Application No. 201710219080.3, dated Mar. 14, 2019, 17 pages.
Advisory Action for U.S. Appl. No. 14/746,328, dated Apr. 22, 2019, 3 pages.

* cited by examiner

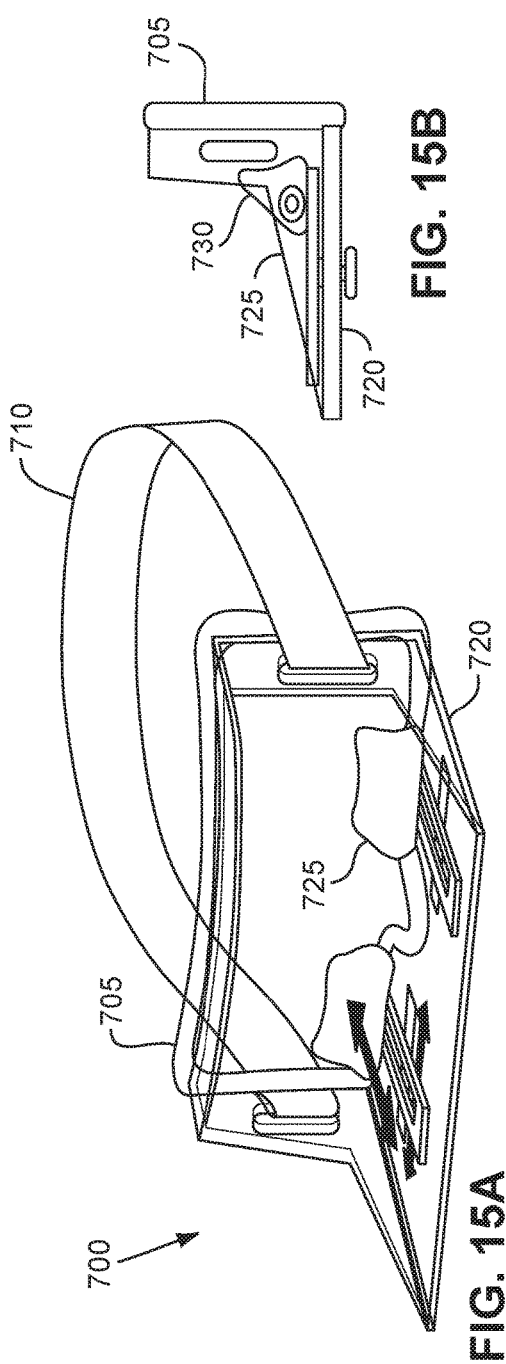

METHODS AND APPARATUSES FOR TREATMENT OF MEIBOMIAN GLANDS

CROSS REFERENCE TO RELATED DOCUMENTS

This application is a Continuation of U.S. patent application Ser. No. 13/183,901, filed Jul. 15, 2011 and entitled Apparatuses for Treatment of Meibomian Glands to Korb et al., issued as U.S. Pat. No. 9,216,028, which is a Continuation of U.S. patent application Ser. No. 11/541,418, filed Sep. 29, 2006 and entitled Treatment of Meibomian Glands to Korb et al., issued as U.S. Pat. No. 7,981,145, which in turn is a Continuation-in-Part of U.S. patent application Ser. No. 11/434,054, filed May 15, 2006 and entitled Method and Apparatus for Treating Meibomian Gland Dysfunction to Korb, et al., issued as U.S. Pat. No. 8,083,787, which claims priority benefit of U.S. Provisional Application 60/700,233, filed Jul. 18, 2005; and is further a Continuation-in-Part of U.S. patent application Ser. No. 11/434,033, filed May 15, 2006 entitled Method and Apparatus for Treating Gland Dysfunction Employing Heated Medium, to Grenon, et al., issued as U.S. Pat. No. 8,915,253; and is further a Continuation-in-Part of U.S. patent application Ser. No. 11/434,446, filed May 15, 2006 entitled Method and Apparatus for Treating Gland Dysfunction to Korb, et al., now abandoned, each of which is hereby incorporated by reference in its entirety.

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

FIELD

This invention relates generally to treatment of mammalian eyes. More particularly, this invention relates treatments of obstruction of meibomian glands by use of various combinations of heat to melt certain obstructions (or melt material binding solid particles forming an obstruction), mechanical action to clear the obstruction and pharmaceutical treatment once the obstruction has been cleared.

BACKGROUND

The human body contains a number of glands including the lacrimal and meibomian glands of the eye, the sebaceous or pilo-sebaceous hair glands on the face and underarms, and the mammary glands in the breasts. These glands may malfunction due to age, irritation, environmental conditions, cellular debris, inflammation, hormonal imbalance and other causes. One common disease state of the eyelid glands is the restriction or stoppage of the natural flow of fluid out of the gland caused by an obstruction.

In the human eye, the tear film covering the ocular surfaces is composed of three layers. The innermost layer in contact with the ocular surface is the mucus layer comprised of many mucins. The middle layer comprising the bulk of the tear film is the aqueous layer, and the outermost layer is a thin (less than 250 nm) layer comprised of many lipids known as "meibum" or "sebum". The sebum is secreted by the meibomian glands, enlarged specialized sebaceous-type glands (hence, the use of "sebum" to describe the secretion) located within both the upper and lower eye lids, with orifices designed to discharge the lipid secretions onto the lid margins, thus forming the lipid layer of the tear film. The typical upper eyelid has about 25 meibomian glands and the lower eyelid has about 20 meibomian glands, which are somewhat larger than those located in the upper lid. The meibomian gland comprises various sac-like acini which discharge the secretion into the main central duct of the gland. The secretion then passes into the orifices which are surrounded by smooth muscle tissue and the muscle of Riolan which are presumed to aid in the expression of sebum. The meibomian gland orifices open onto the lid margin at and around the junction of the inner mucous membrane and the outer skin of the eyelids termed the mucocutaneous junction.

Specifically, as illustrated in the above patent applications, each meibomian gland has a straight long central duct lined with four epithelial layers on the inner surface of the duct. Along the length of the central duct there are multiple lateral out-pouching structures, termed acini where the secretion of the gland is manufactured. The inner lining of each acinus differs from the main central duct in that these specialized cells provide the secretions of the meibomian gland. The secretions flow from each acinus to the duct. While it has not been established with certainty, there appears to be a valve system between each acinus and the central duct to retain the secretion until it is required, at which time it is discharged in to the central duct. The meibomian secretion is then stored in the central duct and is released through the orifice of each gland onto the lid margin. Blinking and the squeezing action of the muscle of Riolan surrounding the meibomian glands are thought to be the primary mechanism to open the orifice for the release of secretion from the meibomian gland.

The upward phase of blinking causes the upper lid to pull a sheet of the lipids secreted by the meibomian glands upward and over the other two layers of the tear film, thus forming a type of protective coating which limits the rate at which the underlying layers evaporate. Thus, it will be seen that a defective lipid layer or an incorrect quantity of such lipids can result in accelerated evaporation of the aqueous layer which, in turn, causes symptoms such as itchiness, burning, irritation, and dryness, which are collectively referred to as "dry eye".

Dry eye states have many etiologies. A common cause of common dry eye states is a disorder where the glands are obstructed or occluded, usually referred to as "meibomian gland dysfunction" (MOD). As employed herein the terms "occluded" and "obstruction" as they relate to meibomian gland dysfunction are defined as partially or completely blocked or plugged meibomian glands, or any component thereof, having a solid, semi-solid or thickened congealed secretion and/or plug, leading to a compromise, or more specifically, a decrease or cessation of secretion. Also with a reduced or limited secretion the meibomian gland may be compromised by the occluded or obstructive condition as evidenced by a yellowish color indicating a possible infection state, or may be otherwise compromised so that the resulting protective lipid protective film is not adequate.

Meibomitis, an inflammation of the meibomian glands leading to their dysfunction, is usually accompanied by blepharitis (inflammation of the lids). Meibomian gland dysfunction may accompany meibomitis, or meibomian gland dysfunction may be present without obvious lid inflammation. Meibomian gland dysfunction is frequently the result of keratotic obstructions which partially or completely block the meibomian gland orifices and/or the central duct (canal) of the gland, or possibly the acini or acini valves (assuming they do in fact exist) or the acini's junction with the central duct. Such obstructions compromise the secretory functions of the individual meibomian glands. More particularly, these keratotic obstructions can comprise combination of bacteria, sebaceous ground substance, dead, and/or desquamated epithelial cells, see, Korb et al., "Meibomian Gland Dysfunction and Contact Lens Intolerance", Journal of the American Optometric Association, Vol. 51, Number 3, (1980), pp. 243-251. While meibomitis is obvious by inspection of the external lids, meibomian gland dysfunction may not be obvious even when examined with the magnification of the slit-lamp biomicroscope, since there may not be external signs, or the external signs may be so minimal that they are overlooked. The external signs of meibomian gland dysfunction without obvious lid inflammation may be limited to subtle alterations of the meibomian gland orifices, overgrowth of epithelium over the orifices, and pouting of the orifices of the glands with congealed material acting as obstructions. In severe instances of meibomian gland dysfunction without obvious lid inflammation the changes may be obvious, including serrated or undulated lid margins, orifice recession and more obvious overgrowth of epithelium over the orifices, and pouting of the orifices.

Hormonal changes, which occur during menopause, and particularly changing estrogen levels, can result in thickening of the oils secreted by the meibomian glands which results in clogged gland orifices. Further, decreased estrogen levels may also enhance conditions under which staphylococcal bacteria can proliferate. This can cause migration of the bacteria into the glands, thus resulting in a decreased secretion rate.

When the flow of secretions from the meibomian gland is restricted due to the existence of an obstruction, cells on the eyelid margin have been observed to grow over the gland orifice thus further restricting sebum flow and exacerbating the dry eye condition. Additional factors which may cause or exacerbate meibomian gland dysfunction include, age, disorders of blinking, activities such as computer use which compromise normal blinking, contact lens wear and hygiene, cosmetic use, or other illness, particularly diabetes.

The state of an individual meibomian gland can vary from optimal, where clear meibomian fluid is produced; to mild or moderate meibomian gland dysfunction where milky fluid or inspissated or creamy secretion is produced; to total blockage where no secretion of any sort can be obtained (see Korb, et al., "Increase in Tear Film Lipid Layer Thickness Following Treatment of Meibomian Gland Dysfunction", Lacrimal Gland, Tear Film, and Dry Eye Syndromes," pp. 293-298, Edited by D. A. Sullivan, Plenum Press, New York (1994)). Significant chemical changes of the meibomian gland secretions occur with meibomian gland dysfunction and consequently, the composition of the naturally occurring tear film is altered, which in turn, contributes to ocular disease which is generally known as "dry eye".

While the tear film operates as a singular entity and all of the layers thereof are important, the lipid layer, which is secreted from the meibomian glands, is of particular significance as it functions to slow the evaporation of the underlying layers and to lubricate the eyelid during blinking which prevents dry eye.

Thus, to summarize, the meibomian glands of mammalian (e.g., human) eyelids secrete oils that prevent evaporation of the tear film and provide lubrication to the eye and eyelids. These glands can become blocked or plugged by various mechanisms leading to so-called "dry eye syndrome". While not the only cause, meibomian gland dysfunction (MGD) is known to be a major cause of dry eye syndrome. The disorder is characterized by a blockage of some sort within the meibomian glands or at their surface preventing normal lipid secretions from flowing from the meibomian glands to form the lipid layer of the tear film.

Such secretions serve to prevent evaporation of the tear film and lubricate the eye and eyelids, hence their absence can cause dry eye syndrome. Obstructions or occlusions of the meibomian glands may be present over or at the orifice of the gland in the main channel of the gland which may be narrowed or blocked, or possibly in other locations including the passages from the acini to the main channel.

It has been theorized that the acini of the glands may have valves at their junction with the main channel of the gland. The inventors theorize that if these valves exist, they may also become obstructed in some instances leading to reduced or blocked flow from the acini. These obstructions or occlusions may have various compositions.

In response to the foregoing, various treatment modalities have been developed in order to treat the dry eye condition, including drops which are intended to replicate and replace the natural tear film, pharmaceuticals which are intended to stimulate the tear producing cells, and various heating devices which are designed to assist in unclogging the meibomian glands. Other techniques involve manual expression of the glands.

Eye drops such as Refresh®, Soothe® and Systane® brand eye drops are designed to closely replicate the naturally occurring healthy tear film. However, their use and administration is merely a treatment of symptoms and not of the underlying cause. Further, the use of drops is generally for an indefinite length of time and consequently, extended use can become burdensome and costly.

Pharmaceutical modalities such as the use of tetracycline have also been suggested to treat meibomian gland dysfunction and one such treatment is disclosed in United States Patent Publication No. US2003/011426 titled "Method for Treating Meibomian Gland Disease", U.S. Pat. No. 6,455,583 titled "Method for Treating Meibomian Gland Disease" to Pflugfelder et al. and PCT Publication No. WO 99/58131 titled "Use of Tetracyclines for Treating Meibomian Gland Disease". However, this treatment has not proven to be universally clinically effective, and it may be unnecessary in cases where meibomian gland dysfunction is the result of obstruction of the gland without infection. The use of corticosteroids have also been proposed to treat meibomian gland dysfunction as disclosed in U.S. Pat. No. 6,153,607 titled "Non-preserved Topical Corticosteroid for Treatment of Dry Eye, filamentary Keratitis, and Delayed Tear Clearance (or Turnover)" to Pflugfelder et al. Again, this proposed treatment appears to treat the symptom of dry eye, as opposed to treatment of the underlying cause. Additionally, the use of topically applied androgens or androgen analogues have also been used to treat acute dry eye signs and symptoms in Keratoconjuctivitis Sicca as disclosed in U.S. Pat. No. 5,958,912 and U.S. Pat. No. 6,107,289 both titled "Ocular Therapy in Keratoconjunctivitis Sicca Using Topically Applied Androgens or TGF-β" and both issued to Sullivan.

Most knowledgeable doctors agree that heat is beneficial in treating MGD. Depending upon the nature of the obstruction, heat may be beneficial in actually melting or loosening the obstructing material, permitting the gland to begin production and excretion of lipids and other fluids more freely.

One modality for the heat treatment of meibomian gland dysfunction is disclosed in European Patent Application serial no. PCT/GB2003/004782 titled "Eyelid Margin Wipes Comprising Chemical Means for Temperature Adjustment". As disclosed in this patent application, a wipe is provided wherein prior to use, a chemical agent is activated that will heat the wipe to about 32° C. to about 40° C. The hot wipe is then applied to the lids and manual expression can then be used to unclog the ducts. This method is not without its drawbacks in that lid irritation can be exacerbated by non-specific heating.

Another method of heating the eyelids and meibomian glands uses near infrared (NIR) radiation. More specifically, two hard eye patches were attached to an eye mask according to the pupillary distance of the subject. The eye mask was held in place by an elastic headband. Each patch employed 19 light emitting diodes, emitting near infrared radiation from 850 nm to 1050 nm, with a peak at 940 nm. The device produced 10 mW/cm$^2$ of energy operating on electrical power. Goto, E., et al., Treatment of Non-Inflamed Obstructive Meibomian Gland dysfunction by an Infrared Warm Compression Device, British Journal of Ophthalmology, Vol. 86 (2002), pp. 1403-1407. This device is designed as a non-contact infrared heating mask using IR light emitting diodes. However, there are many potential problems with use of an IR heating mechanism. For example, the IR Heat can penetrate beyond the eyelid into the cornea which is undesirable, and could ultimately cause cataracts or other damage. Additionally, the IR mask heater places no pressure whatsoever on the eyelid (despite the description as a compression device) which we have determined is useful to expel the blockage. Moreover, tests conducted on a sample of this mask revealed that in spite of the potential dangers, the mask produced very little actual heat.

United States Patent Publication US2004/0237969 titled "Therapeutic Eye and Eye Lid Cover" comprises a pair of goggles that are adapted to deliver heated saturated air to the eyelids and particularly to the meibomian glands, again to heat the gland. Heat treatment of the eyes is also discussed in the article titled "Tear Film Lipid Layer Thickness and Ocular Comfort after Meibomian Therapy via Latent Heat with a Novel Device in Normal Subjects by Mitra et al, published in Eye, (2004) at pages 1-4.

United States Patent Publication US2003/0233135 titled "Method and Apparatus for Preventing and Treating Eyelid Problems" to Yee attempts to clear the plugged meibomian glands by means of electrical stimulation of the muscle of Riolan which the invention presumed to aid in the expression of the meibomian gland secretion.

SUMMARY OF CERTAIN EMBODIMENTS

It is an object of certain embodiments consistent with the present invention to provide a method for treatment of mammalian eyelids.

It is another object of certain embodiments consistent with the present invention to provide a method of treatment that first produces a flow of lipids from the meibomian glands of the upper and/or lower eyelids of either or both eyes in order to aid in the clearing of certain types of obstructions that may be present in or about the meibomian glands, followed by pharmacological treatment to assist in maintaining the flow of lipids or otherwise assist in the promoting lubrication of the eyes.

In one embodiment consistent with the present invention a method of treating mammalian meibomian glands involves clearing the glands by applying a regulated heat to an eyelid containing the meibomian glands to a temperature adequate to melt obstructions in the meibomian glands, thereby placing the obstruction in a fluid or suspension (melted) state, and maintaining the heat for a time period adequate to melt the obstructions and place the obstructions in the fluid or suspension (melted) state. The glands can then be mechanically treated to express fluid from the glands, wherein the treating is carried out either during the time period or after the time period but while the obstruction remains in the fluid or suspension state. In most instances, this should be carried out within about 90 seconds of the end of the time period. Subsequent pharmacological treatment of the glands by use a pharmacological agent (topical or systemic) can then be used to assist in maintaining proper flow of lipids from the glands or otherwise assist in the promoting lubrication of the eyes.

In accordance with certain embodiments, the time period can be approximately 10 to 60 minutes, and approximately 15 minutes is generally suitable for mild to moderate cases of MGD. In more severe cases, treatments of 30-45 minutes may be required, and for very severe cases, up to and beyond 60 minutes of heat treatment may be needed. These times assume a target temperature of 44-47 degrees with 45 degrees C. being preferred, and may possibly be reduced somewhat for higher temperatures or extended 30 somewhat for lower temperatures. Temperatures can range from 37 degrees Celsius and up.

In certain embodiments, the mechanical treatment is carried out by at least one of application of constant pressure, vibratory energy, mechanical energy, pulsating mechanical stimulation, squeezing, milkingly expressing the fluid from one or more of the glands while simultaneously applying heat, or applying vibratory stimulation to the eyelid while simultaneously applying heat.

In another embodiment, a method of treating meibomian gland dysfunction in a mammal wherein an occlusion blocks at least a portion of the flow of naturally occurring secretions out of a gland channel orifice involves applying a regulated heat source proximate to the gland channel orifice for a selected time and at a selected temperature adequate to soften or liquefy at least a portion of the occlusion; mechanically treating the gland channel orifice while the at least a portion of the occlusion remains softened or liquefied such that at least a portion of the occlusion is removed; subsequently treating the mammal with a pharmacological agent which promotes the free flow of lipids from the meibomian gland or otherwise assist in the promoting lubrication of the eyes.

In another embodiment, a method of treating meibomian gland dysfunction in a mammal wherein an occlusion blocks at least a portion of the flow of naturally occurring secretions out of a gland channel orifice involves applying a regulated heat source proximate to the gland channel orifice for a selected time and at a selected temperature adequate to loosen, breakup, fracture, soften or liquefy at least a portion of the occlusion; mechanically treating the gland channel orifice prior to reversal of the effects of the application of the regulated heat source such that at least a portion of the occlusion is removed; subsequently treating the mammal with a pharmacological agent which promotes the free flow of lipids from the meibomian gland or otherwise assist in the promoting lubrication of the eyes.

The above overviews are intended to illustrate exemplary embodiments which will be best understood in conjunction with the detailed description to follow, and are not intended to limit the scope or meaning of the appended claims.

BRIEF DESCRIPTION OF THE DRAWINGS

Certain illustrative embodiments illustrating organization and method of operation, together with objects and advantages may be best understood by reference detailed description that follows taken in conjunction with the accompanying drawings in which:

FIG. 15A is a perspective view of another embodiment of the meibomian gland treatment apparatus in the form of the hydro-oculator according to the present invention.

FIG. 15B is a side view of the hydro-oculator of FIG. 15A.

FIG. 15C is a schematic side view of the hydro-oculator according to the present invention in place against the lower eyelid.

FIG. 15D is a schematic side view of the hydro-oculator according to the present invention in place against the lower eyelid and showing the fluid filled bladder beginning to expand.

FIG. 15E is a schematic side view of the hydro-oculator according to the present invention in place against the lower eyelid and showing the fluid filled bladder in a further expanded state.

DETAILED DESCRIPTION

Figure 1:
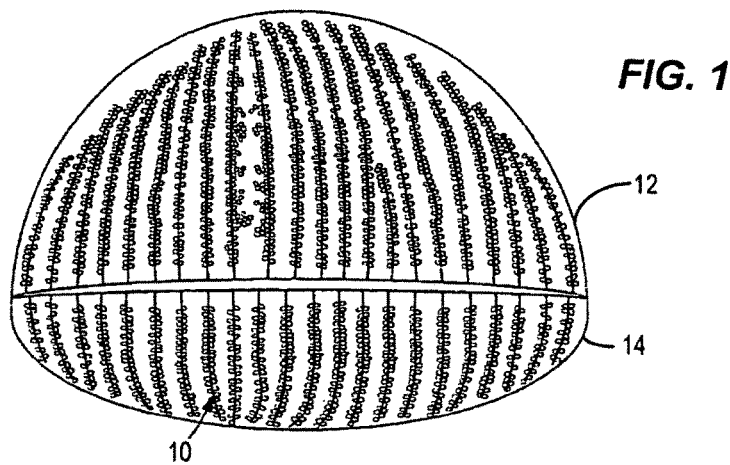
FIG. 1 depicts upper and lower human eyelids showing the meibomian glands.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically. The term "program" or "computer program" or similar terms, as used herein, is defined as a sequence of instructions designed for execution on a computer system. A "program", or "computer program", may include a subroutine, a function, a procedure, an object method, an object implementation, in an executable application, an applet, a servlet, a source code, an object code, a shared library/dynamic load library and/or other sequence of instructions designed for execution on a computer system.

Reference throughout this document to "one embodiment", "certain embodiments", "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; Band C; A, B and C". An exception to this definition will occur only when a combination of elements, functions, steps or acts are in some way inherently mutually exclusive.

As noted above, meibomian gland dysfunction (MGD) is known to be a major cause of dry eye syndrome. The disorder is characterized by a blockage of some sort within the meibomian glands preventing normal lipid secretions from flowing through the orifices and out of the glands to the tear film. Obstructions or occlusions of the meibomian glands may be present at the orifice of the gland, the main channel of the gland, or possibly in other locations including the main channel of the gland which may be narrowed or blocked. It has been theorized that the acini of the glands may have valves at their junction with the main channel of the gland, and that these valves may be obstructed in some instances-leading to reduced or blocked flow from the acini. These obstructions or occlusions may have various compositions.

Figure 2:
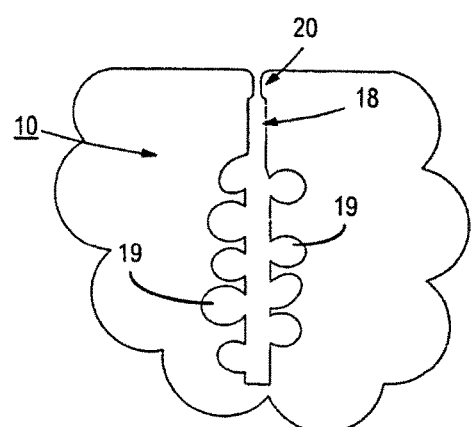
FIG. 2 is a cutaway view of an illustrative meibomian gland 20.

Referring now to FIG. 1, the location of the meibomian glands 10 are shown on the upper and lower eyelids 12 and 14 respectively. As briefly stated herein above, the upper lid contains about 25 meibomian glands and the lower lid contains about 20 meibomian glands, with significant variation. As shown in cross-sectional view of one gland 10 in FIG. 2, each gland includes a central duct or channel 18 into which the secretion flows from acini 19 and an orifice 20 which opens on to the eyelid margin and through which the secretion flows in order to be added to the tear film upon blinking. It will be seen that the glands are of different size, depending upon the location in the eyelid and that the orifice 20 is narrower than the central duct 18.

Figure 3:
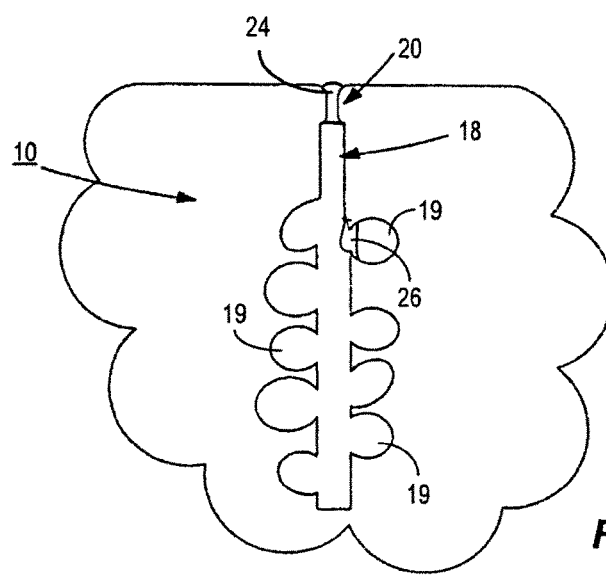
FIG. 3 is a cutaway view meibomian gland 20 illustrating several obstructed areas.

Obstruction composition will vary with the etiology which produced it. However, the obstruction will, in most cases observed to the present, be a combination of, dead cells, bacteria, desquamated cells, and desquamated cells aggregating in keratotic clusters, milky fluid, inspissated or creamy secretions, or any combination of the foregoing in solid, semi-solid and thickened forms. Referring to FIG. 3, a simplified view of exemplary obstructions to gland 10 are depicted. In this example, which is by no means necessarily representative' of all meibomian gland obstructions, as explained above, a solid or semi-solid or thickened plug 24 is depicted which is fully occluding the orifice 20 of gland 10. Another obstruction 26 is shown at a junction from one of the acini with the central duct. As previously noted, this may be the site of a valve in the gland structure, but embodiments consistent with the present invention should not be limited by theories of the actual meibomian gland structure.

A number of treatment techniques have been proposed to restore these glands to normal functionality, but most doctors agree that heat is beneficial in treating MGD. Depending upon the nature of the obstruction, heat may be beneficial in actually melting or loosening the obstructing material or material binding solid particles to form the obstruction, permitting the gland to begin production and excretion of lipids and other fluids more freely. While the heat treatment methods described in the Background section hereof have been found to have many drawbacks, the heating techniques described in the above referenced copending applications have been found effective and beneficial. Generally speaking, these devices produce a regulated heating of the eyelid (as measured at the outer surface thereof) by direct contact with the eyelids to a therapeutic temperature of greater than 37 degrees Celsius, and more preferably between about 44 and 47 degrees Celsius with a target temperature of 45 degrees Celsius. However, other devices may be used which are placed proximate to the eyelids to provide heat to the meibomian glands.

The outside skin surface of the human eyelid has been observed to be approximately 1-2 degrees Celsius cooler than body temperature, with some variation. Increasing the temperature to at least 37 can begin to provide therapeutic effect for milder cases of MGD. One preferred range for treatment is 44 to 47 degrees Celsius, with a target of 45 degrees Celsius has been found effective and comfortable to the patient. In certain embodiments, the mechanical energy treating is carried out during or immediately after the end of the time period, and preferably with a heated instrument so as to maintain the more fluid state of the obstruction. Mechanical energy treatment can be carried out by any mechanism that induces mechanical pressures, including but not limited to vibratory, milking, mechanical pulsing pressure, squeezing and other actions to express fluids from the glands and/or dilate the duct or orifice of the meibomian gland. The mechanical energy can take any form that applies mechanical pressure on the meibomian glands to assist in pushing the blockage or obstruction out of the gland while the obstruction is softened by heat. Even higher temperatures (e.g., 50-55 degrees Celsius) can be used (or pulsed for short periods), especially if the eyelid has been anesthetized, in which case much hotter treatment for shorter time can be used without permanent injury to the patient. Generally, higher temperatures can be used for shorter periods of time. Moreover, the temperature and time used should be individualized based on the severity of the condition and the tolerance of the patient. It has been found that lighter skinned patients can generally tolerate less heat than darker skinned patients, and darker skinned patients tend to exhibit less inflammation as a result of exposure to the heat. Treatment times and/or temperature can be adjusted to account for these differences. Each of the above temperatures refers to the temperature as measured at the outer surface of the eyelid.

Also, in certain embodiments, the patient is more comfortable when the treatment begins at a lower temperature and the temperature is raised over time. Hence, the temperature should be regulated, where regulation should be interpreted to mean that the actual temperature applied at the outer surface of the eyelid is controlled or regulated in a manner that is repeatable. The temperature profile for heat application may be a constant temperature, or may have ramp-ups, ramp-downs, peaks, valleys, can be pulsed, or can be modulated with various characteristics, etc., but such profile should be regulated so as to be repeatable. It has also been found that modulating the temperature can result in a higher average temperature than a constant temperature, and may be useful in some applications.

This temperature can be maintained at a therapeutic temperature for a treatment period of approximately 10-60 minutes (or even beyond have been found safe and useful for some patients). Either during or after such treatment by controlled heat, mechanical expression of lipids and other fluids from the meibomian glands has been found to clear obstructions which have essentially melted or been placed in a suspension state (by virtue of melting materials binding solids together). The above applications disclose devices which generally apply a milking action to the eyelid to express the fluids or suspensions or to otherwise mechanically stimulate the movement of fluids from the glands—such fluid now including melted or suspended materials causing the obstructions or occlusions. In some instances, just gentle continuous force applied to the eyelid will assist in expression of the fluids and suspensions, while in others vibration can be used simultaneously or immediately after the heating. For purposes of this document, the term "melted" is to be interpreted to be inclusive of states in which solid particles remain suspended within a liquid fluid.

In certain embodiments, such devices that apply regulated heating of the eyelids are disclosed in U.S. patent application Ser. No. 11/434,054, filed May 15, 2006 and entitled Method and Apparatus for Treating Meibomian Gland Dysfunction to Korb, et al and U.S. patent application Ser. No. 11/434,033, filed May 15, 2006 entitled "Melting Meibomian Gland Obstructions", to Steve Grenon, et al. which are hereby incorporated by reference. In certain embodiments, that device utilizes a heater unit having a heating element that produces heat when an electrical signal is applied thereto. A temperature regulator applies the electrical signal to the heating element in order to achieve heating of the heating element to a specified temperature range. An eyelid interfacing mechanism couples the heater unit to the eyelid to achieve regulated heating of the eyelid within the specified temperature range.

Such a device provides regulated heating to a therapeutic temperature. Conventional hot compresses and the IR heating mechanisms described above background do not provide regulated controlled heating at a therapeutic temperature and are less effective than the regulated heat applied using the devices described in the above-referenced patent applications that are incorporated herein.

In another embodiment disclosed in this patent application, an apparatus that provides controlled heat to at least one of a patient's eyelids has a heater unit, and the heater unit having: a heating element having first and second surfaces that produces heat when an electrical signal is applied thereto; a thermal heat sink, coupled to the first surface of the heating element in order to transfer heat from the heating element to the eyelid; an insulator coupled to the second surface of the heating element in order to reduce heat loss from the second surface; and a back plate that couples to the insulator. A temperature regulator applies the electrical signal to the heating element in order to achieve heating of the heating elements to a specified temperature range. Goggles suitable for attaching to the patient's head and covering the eyelid of the patient with a lenspiece are provided with the lenspiece having a threaded aperture therein. A threaded shaft passes through the threaded lenspiece and coupled to the heater unit at the back plate so that the heater unit can be moved into contact with the eyelid by screwing the shaft into the aperture until contact with the eyelid is achieved.

Many variations in these embodiments are possible including, but not limited to, providing a sensor that senses temperature and provides temperature information to the temperature regulator. In certain embodiment the eyelid interfacing mechanism comprises goggles that are adjustably coupled to the heater unit in order to move the heater unit to achieve contact with the eyelid. The goggles may be adjustably coupled to the heater unit by a threaded connection so that a position of the heater unit can be adjusted by a threading action. In certain embodiments, the heater unit has a thermal heat sink, coupled to a surface of the heating element in order to transfer heat from the heating element to the eyelid. The thermal heat sink may be, for example, at least one of a thermally conductive rubber member, a thermally conductive silicon member, an encapsulated fluid containing member, and a solid conductive member. A thermally conductive gel, cream or liquid can be placed between the heat sink and the eyelid to enhance thermal conduction from the thermal heat sink to the eyelid.

In certain embodiments, the heater unit may have an insulator coupled to a surface of the heating element in order to reduce heat loss from the heating unit in a direction other than a direction toward the eyelid. The thermal insulator may be one of a non-thermally conductive foam element, a non-thermally conductive rubber element, and a non-thermally conductive solid element in certain embodiments. The temperature regulator may apply a pulse width modulated electrical signal to the heating element in order to regulate the heat produced thereby, and the pulse width modulated electrical signal may be produced under control of the control processor.

In certain embodiments, the temperature regulator may incorporate a switch that selectively applies the electrical signal to the heating element in order to regulate the heat produced thereby. The electrical signal may be at least one of a current and a voltage that is selectively applied to the heating element under control of a control processor. The heater unit may have a flexible portion that contacts the eyelid in order to conform to the eyelid or may have a rigid portion that contacts the eyelid, and wherein the rigid portion is shaped to conform to the shape of the eyelid, or a combination thereof. The heater unit may have an adhesive for attaching the heater unit directly to the eyelid or may be attached to the eyelid by use of adhesive tape.

In certain embodiments, a user interface permits a user to establish at least one of a time and a temperature for the treatment. In certain embodiments, a vibration generator generates vibration of the eyelid to stimulate secretion from the meibomian glands, wherein the vibration generator may impart mechanical energy to the eyelid having both an amplitude and frequency.

Other heating and/or pressure inducing devices are disclosed in the above-referenced patent applications which are incorporated herein by reference.

Hence, in view of the above, either immediately after treatment with heat, or during such heat treatment, mechanical treatment using, for example, constant force, squeezing (e.g., by manual expression or otherwise), milking action or vibration can be applied to the eyelid to stimulate clearing of the fluids or suspensions from the meibomian glands. If mechanical treatment is carried out after heat treatment, it should be carried out immediately thereafter while the obstructive material of the meibomian gland is in a melted state.

Figure 4:
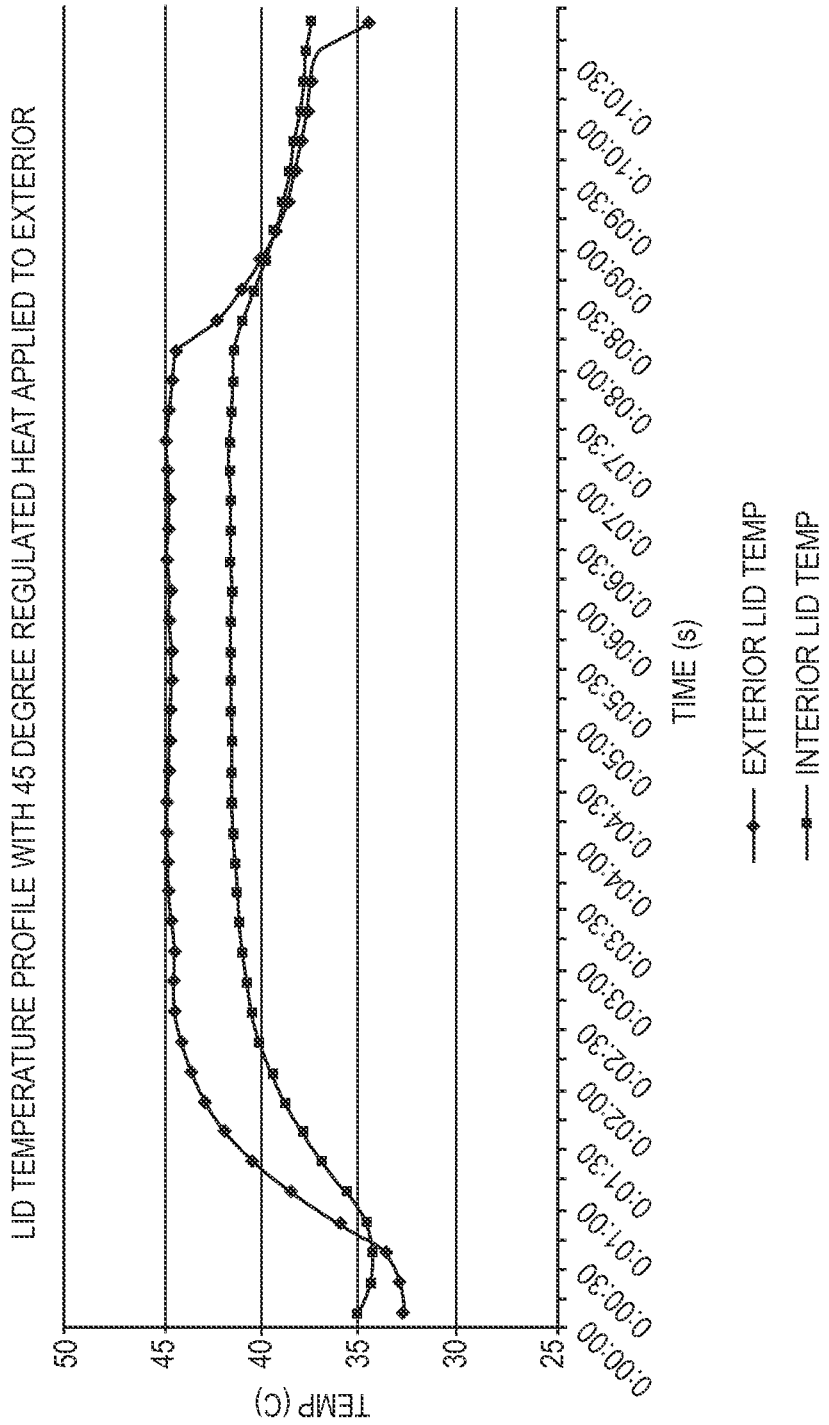
FIG. 4 is a graph of inner and outer surface temperatures of a patient's eyelid while the outer surface of the eyelid is heated to about 45 degrees C.

Referring now to FIG. 4, a graph depicts the inner surface of an eyelid and an outer surface of an eyelid when a source of constant heat at about 45 degrees C. was applied to an example subject patient. It should be noted that the circulatory system attempts to regulate the temperature of the eyelid, and blood flow increases with the application of heat. For this patient, it took approximately 4 minutes for the eyelid's outer surface to reach about 45 degrees Celsius, and the inner surface of the eyelid never reached this temperature—presumably because of the body's heat regulatory mechanisms. Hence, if a 45 degree constant heat source is used, it may take at least about 4 minutes to stabilize eyelid temperature and reach a therapeutic temperature.

It is also noted from this graph, that when the heat source is removed from the eyelid, the temperature drops very quickly to body temperature. In virtually all cases, this temperature will drop within 2-3 minutes, but more commonly, only about 30 seconds to 90 seconds are required for the patient's eyelid temperature to drop. In this example, the temperature dropped in temperature very quickly over the first thirty seconds after removal of the heat. During this short time period, some or all of the melted obstruction may re-solidify. Hence, if manual expression techniques are to be carried out subsequent to application of heat, the manual expression should follow immediately, or within about 90 seconds—with shorter intervals being preferred, e.g., within 30 seconds, or in any event, prior to reversal of the effects of the application of the regulated heat source such that at least a portion of the occlusion is removed. It will thus be clear from this graph that prior techniques of using warm compresses may be substantially less effective if manual expression does not follow within an extremely short period of time. Moreover, if the compresses cool below a therapeutic level prior to manual expression, they may provide minimal benefit to a patient suffering from substantial obstruction.

It has been discovered that the problem with most pharmacological treatment modalities for dry eye syndrome is that the pharmacological agent is unable to affect MGD when the disorder involves obstructions of the gland. That is, the currently known pharmaceutical treatments simply cannot unclog the meibomian glands to permit flow of lipids. While antibiotic treatment, steroid treatment, or other pharmacological treatments may be useful for other causes of dry eye, they have been found ineffective (or at most, to provide temporary symptomatic relief) when obstruction of the meibomian glands is involved. While many pharmacological agents may be useful in promoting lipid production and flow of the meibomian glands, such lipid production is not effective, and may be counterproductive if the secretion cannot get out of the gland. In fact, promoting lipid production may cause more meibomian difficulties and inflammation of the glands.

Other pharmacological agents may assist in promoting tear production or otherwise assisting in the lubricating function of the eye by promoting an improvement in the tear film. Used alone, such treatments may be ineffective or only partially effective, whereas, used after clearing of the meibomian glands may restore normal or near normal production of all components of the tear film. Hence, many pharmacological agents may be appropriate for further enhancement of the tear film and may be extremely beneficial once the meibomian glands are returned to more normal function.

Hence, once flow has been restored to the meibomian glands by heat and manual treatment (e.g., pressure during or after treatment, vibration, pulsation, manual expression, etc.), treatment with various pharmacological agents can be beneficial to maintaining the flow of lipids from the glands. Hence, with reference to FIG. 5, a treatment regimen is described starting at 100, after which a controlled heat such as produced by the various apparatus described in the above-referenced and incorporated by reference patent applications is applied to the eyelids at 104. The preferred heat is greater than 37 degrees Celsius, with a preferred range of heat between approximately 44-47 degrees Celsius, with a target of 45 degrees Celsius. However, greater temperatures Celsius for shorter periods of time will provide therapeutic benefit, with the possible side effect of minor skin burns that do not cause lasting damage. Below this temperature range, treatment tends to be less effective or ineffective. Temperatures above this range can cause substantial patient discomfort, injury to the eyelids and possibly the eye. At higher temperatures within the range, the patient may find the heat to be somewhat uncomfortable, but the treatment time• can be reduced and the discomfort can be moderated with anesthetic. Lower temperatures in the range are effective but generally take a longer heating period.

As a rule of thumb starting point, fifteen minutes at a relatively constant 45 degrees generally works well for many patients with mild to moderate MGD without undue patient discomfort. Time ranges from about 10-60 minutes or even beyond may be used depending upon the severity of the MGD condition, the temperature, anesthetic used and patient tolerance. In experiments, times beyond one hour were used without apparent adverse effects.

Once the heat treatment is completed (and/or during the heat treatment), mechanical force can be applied at 108 in any of the above mechanical modalities discussed to express the fluids or suspensions from the meibomian glands while the obstructions are in the melted state. When expression of the glands is used, it is preferable that any instrument used in the expression process be heated so as to simultaneously apply or assist in maintaining heat to the glands at the time of expression.

While manual expression of the gland can be painful and is invasive with inconsistent results when used alone due to variations in manual control and/or manipulation, and while this method of treating MGD can also be quite uncomfortable to the patient because it requires the physician to squeeze the glands, this technique may prove useful as a step in the process used selectively in difficult cases. There are about 45-50 glands between the upper and lower lid, therefore, it is very time consuming to squeeze each gland and therefore inefficient for the physician and uncomfortable for the patient to endure. However as noted, it may be beneficial in combination with automated expression devices to assist in further clearing severely obstructed glands to enhance the normal flow of lipids flowing through the orifices and out of the glands to the tear film. After heat treatment, the expression of secretions from an obstructed gland is generally dramatically more effective with less patient discomfort and better results, than if used alone. As noted previously, when expression of the glands is used, it is preferable that any instrument used in the expression process be heated so as to simultaneously apply heat or assist in maintaining heat to the glands at the time of expression.

Once the occlusions and other foreign substances have been cleared from the meibomian glands at 104 and 108 and lipid flow is restored, the meibomian glands can be treated with any of a variety of pharmacological agents, either topical or systemic, in order to minimize inflammation of the glands, clear infections, prevent further blockages, thin the lipids, promote production of tears, enhance the composition of the tear film, or any other pharmacological modality that promotes the free flow of the lipids or enhanced lubrication of the eye at 112. Pharmacological treatment may be carried out either for a short duration (e.g., to clear an infection or inflammatory condition), or for ongoing therapy (e.g., as in pharmacological agents that thin the lipids, reduce inflammation or treat other modalities of dry eye syndrome). This process ends at 116.

Many pharmacological agents have been proposed for treatment of dry eye syndrome, any of which may be effective or more effective upon clearing of obstructions within the meibomian glands. Some of the pharmacological agents that may be utilized include, but are not limited to: antibiotics such as topical or oral tetracycline and chemically modified tetracycline, testosterone, topical or oral corticosteroids; topical androgens or androgen analogues, omega 3 fatty acid compounds such as fish oils, laennec, enzymes that promote lipid production, agents that stimulate production of enzymes that promote lipid production, and any agent which acts as a secretagogue to enhance meibomian gland secretion or secretion of other tear components. Androgen and androgen analogues and TGF-β have been reported to act as a secretagogue to enhance meibomian gland secretion, agents that replace or promote production of any tear component, and there are likely many others. These compounds are illustrative examples of appropriate pharmacological agents, but those skilled in the art will appreciate that other pharmacological compounds may be utilized upon consideration of the present teachings. It is further noted that multiple modalities may be involved in causing dry eye syndrome, but treatment of only one modality may not result in full resolution. Hence, the restoration of normal or near normal lipid flow from the meibomian glands may be only a part of the solution—with pharmacological treatment of the other modality or modalities of the disease restoring a normal tear film. However, when significant MG dysfunction is involved, treatment of the other modalities alone is likely to be less than satisfactory.

A variation of the above treatment is described in connection with FIG. 6 starting at 130, after which a controlled heat such as produced by the various apparatus described in the above-referenced and incorporated by reference patent applications is applied to the eyelids at 104 as in the prior treatment method. The preferred range of such heat is again between approximately 44-47 degrees Celsius, with a target of 45 degrees Celsius. Again, time ranges from about 10 to 60 minutes and beyond may be used, depending upon severity of the condition, the treatment temperature and patient tolerance.

In this embodiment, during the heat treatment, mechanical force can be applied at 138 in any of the above mechanical modalities discussed, including those referenced and incorporated by reference, to express the fluids or suspensions from the meibomian glands while the obstructions are in a liquid or suspension state during application of the heat.

Depending upon the patient response to heat in combination with simultaneous mechanical force at 138, additional force can be applied immediately subsequent to removal of the heat at 142. In this case, it is also preferred that heat be maintained during the time of expression or force being applied as described. That is, it is preferred that any probe or other instrument used during the expression be heated to help maintain the obstruction in a liquid or suspension state. Such force can be manually applied by squeezing the eyelids at appropriate locations where obstructions appear to remain, or automated mechanical means may be employed if available.

Once the occlusions and foreign substances have been cleared from some or all of the meibomian glands at 104, 138 and 142, the meibomian glands can be treated with any of a variety of pharmacological agents, either topical or systemic, in order to minimize inflammation of the glands, clear infections, prevent further blockages, thin the lipids or any other pharmacological modality that promotes the free flow of the lipids or otherwise promote an improved tear film at 112 as before. As noted, pharmacological treatment may be carried out either for a short duration (e.g., to clear an infection or inflammatory condition), or for ongoing therapy (e.g., as in pharmacological agents that thin the lipids, improve the tear composition, or reduce inflammation). This process ends at 150.

Figure 5:
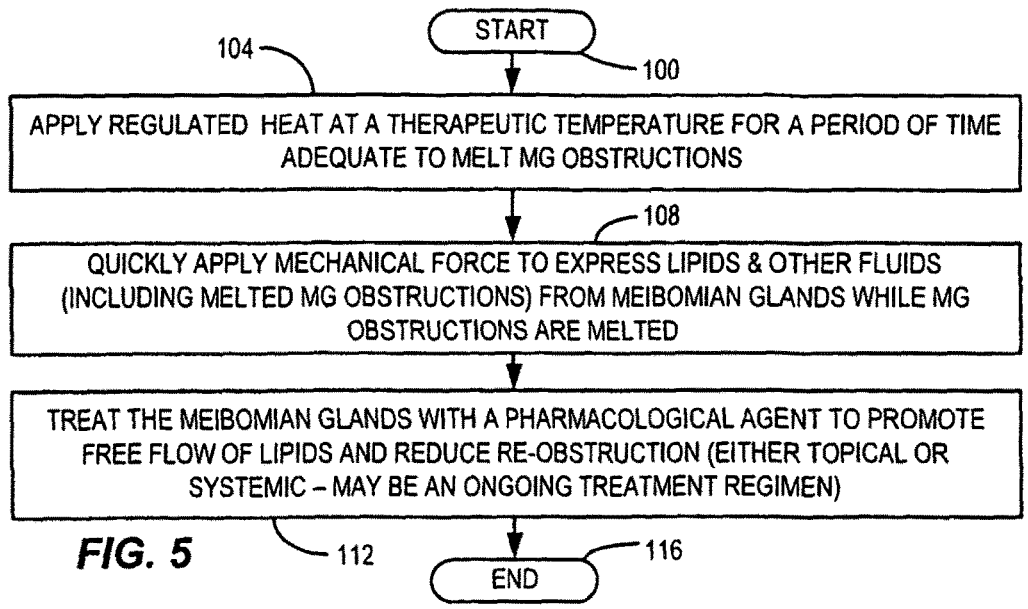
FIG. 5 is a flow chart depicting a treatment process consistent with certain embodiments of the present invention.
Figure 6:
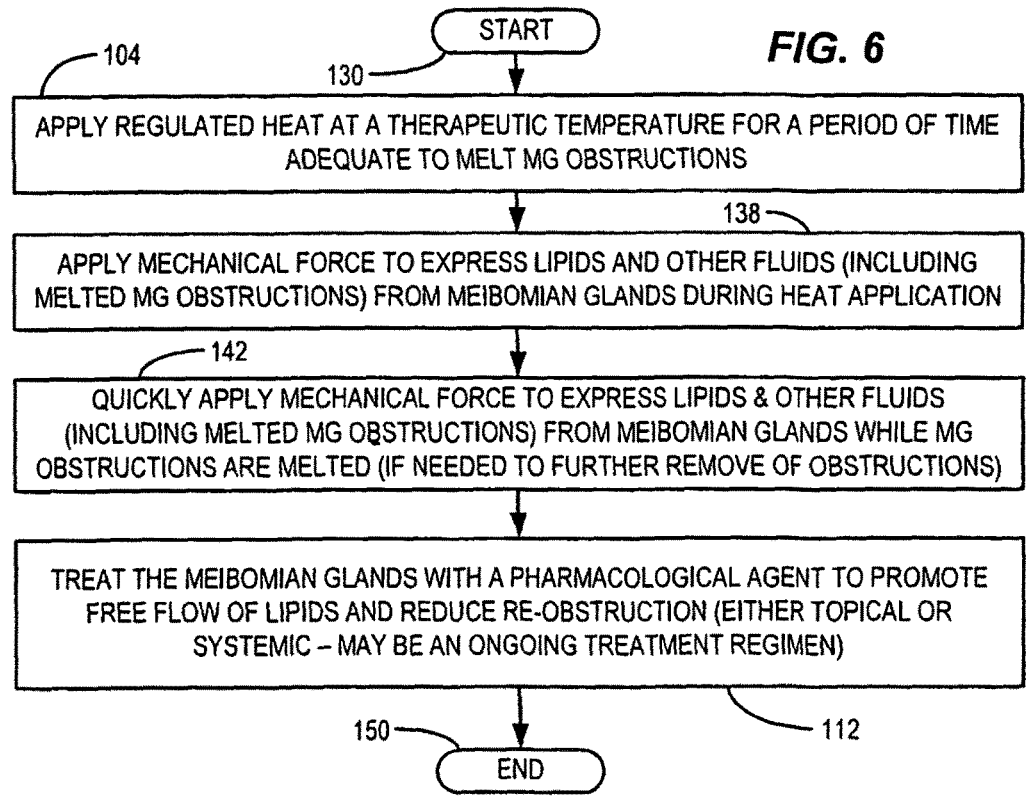
FIG. 6 is a flow chart depicting another treatment process consistent with certain embodiments of the present invention.

The above processes, whether involving the process of FIG. 5 or FIG. 6, may be repeated or interchanged at time intervals as needed to create or maintain proper flow from the meibomian glands. Such treatments, or portions thereof, may need to be periodically repeated for some patients in order to keep the lipids flowing from the meibomian glands.

Thus, in accordance with certain embodiments consistent with the present invention, a method of treating mammalian meibomian glands involves clearing the glands by applying a regulated heat to an eyelid containing the meibomian glands to reach a temperature adequate to melt obstructions in the meibomian glands and maintaining the heat for a time period adequate to melt the obstructions and place the obstructions in a fluid or suspension (melted) state. The glands can then be mechanically treated to express fluid or suspension from the glands, wherein the mechanical treatment is carried out either during the time period or after the time period but while the obstruction remains in the melted state. The process may be enhanced by a heated treatment device for applying the force to maintain the temperature and the melted state of the obstructive material. Subsequent pharmacological treatment of the glands by use of a pharmacological agent (topical or systemic) can then be used to assist in maintaining proper flow of lipids from the glands.

In accordance with certain embodiments, the time period can be approximately 10 to 60 minutes, and approximately 15 minutes is generally suitable for mild to moderate cases. The temperature should be greater than 37 degrees Celsius and the preferred range is approximately 44 to 47 degrees Celsius with a target of 45 degrees Celsius at the eyelid's outer surface has been found effective and comfortable to the patient. In certain embodiments, the mechanical treating is carried out as soon as possible after the heating, and preferably within about 30-90 seconds, so that the obstruction will remain in a melted state during the expression process. In other embodiments, the mechanical treatment is carried out by at least one of application of constant pressure, squeezing, milkingly expressing the fluid or suspension from one or more of the glands while simultaneously applying heat, or applying vibratory stimulation to the eyelid while simultaneously applying heat. Many variations and alternative embodiments will occur to those skilled in the art upon consideration of the present teaching.

Figure 7A:
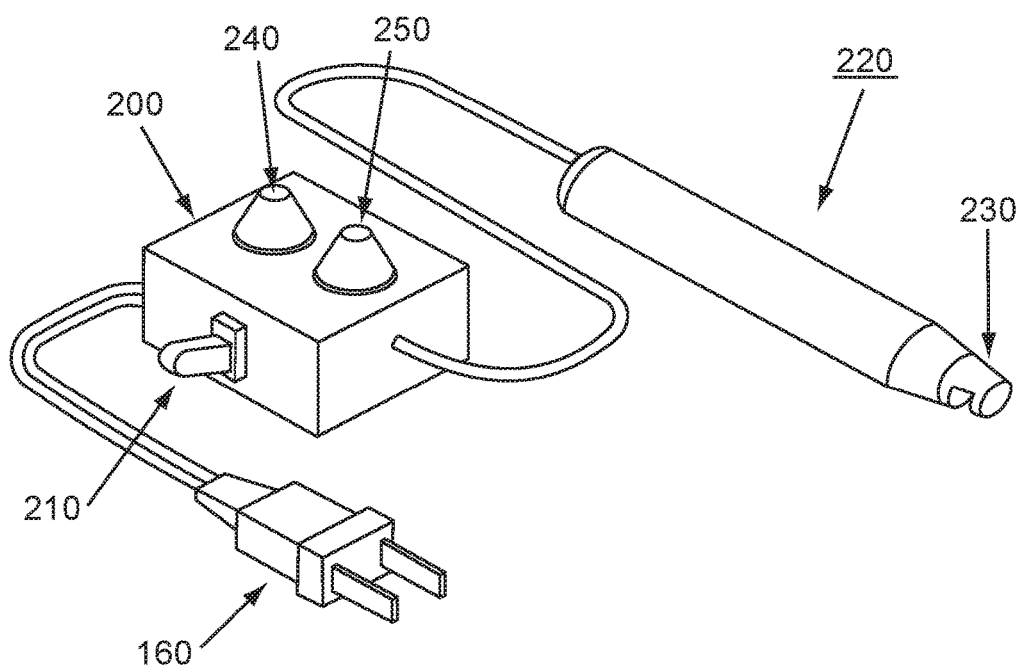
FIG. 7A is a perspective view of a system for clearing obstructed meibomian glands.

An apparatus for unplugging the obstructed gland channel C is schematically illustrated in FIG. 7A. The apparatus comprises a power source 160 which may be direct current (battery powered) or alternating current (wall socket) as desired. The power source 160 is connected to a controller, generally indicated at 200, which includes a power on/power off switch 210. The controller 200 includes a means 220 for applying an external force to the gland to loosen the obstruction. The means 220 includes a probe 230, which is adapted to vibrate at a preselected frequency at preselected amplitude. The probe 230 may vibrate at sonic or ultrasonic frequencies as needed. In addition, means for varying the frequency 240 and amplitude 250 of the probe output, well known to those skilled in the art, are provided. The means 220 for applying the regulated external force or regulated energy to the obstruction may also include fluid jet, air fluid, water fluid, microwave energy, needles, micro-needles, laser energy, RF energy, aspiration, suction, vacuum, pressure, piezoelectric, and compression.

Figure 7B:
FIG. 7B is a broken away side view of the probe tip employed in the embodiment of FIG. 7A.
Figure 8A:
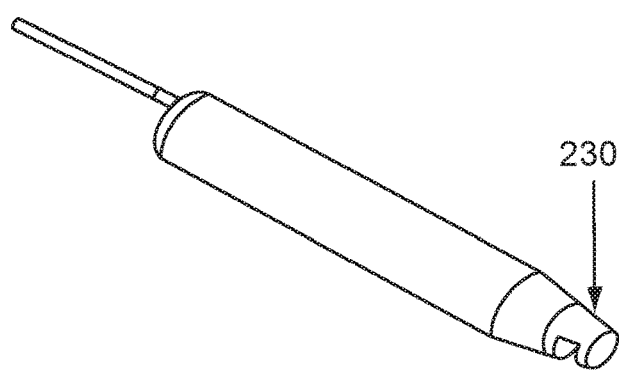
FIG. 8A is a perspective view of a second embodiment of the probe tip according to the present invention.
Figure 8B:
FIG. 8B is a broken away side view of the probe tip of FIG. 8A.
Figure 8C:
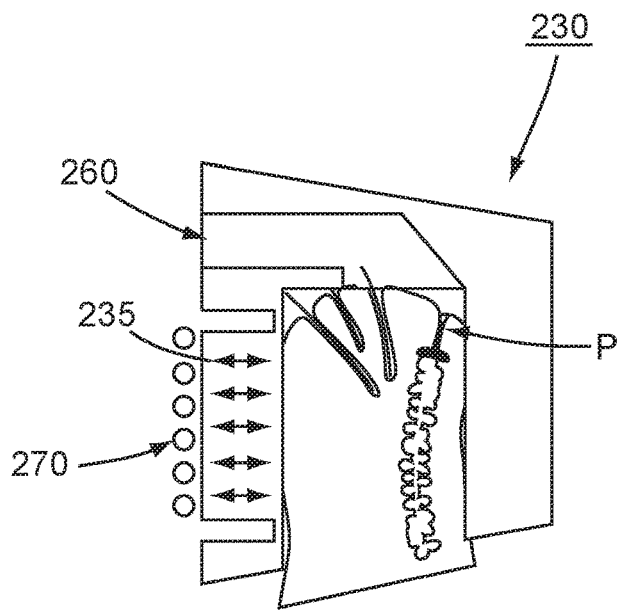
FIG. 8C is a broken away side view of the probe tip of FIGS. 7A and 8A in place on an eye lid.

Turning now to FIG. 7B, a small ultrasonic probe 230 (and specifically the probe tip) is illustrated in FIG. 8C in place on the eyelid. The probe 230 is adapted to deliver ultrasonic vibrational energy through the skin into the obstruction P in order to loosen, liquefy, and/or fracture the obstruction. More specifically, by tuning the probe output so that the obstruction P resonates (by adjusting the frequency and amplitude of the signal) energy is efficiently transferred to the obstruction and sympathetic vibration of the obstruction P occurs with minimal energy transfer to the surrounding tissues. In some instances, vibration alone may be sufficient to change the characteristics of the obstruction P such that vigorous blinking may express the obstruction remnants.

In addition to vibration alternative force, energy, aspiration and/or chemical/pharmacological agents can be used to open up the channel C. The probe may be further equipped with aspiration means 260 (best illustrated in FIG. 8C for introducing aspiration, suction or vacuum into the gland channel C to evacuate the obstruction remnants. Alternatively, heat and aspiration may be employed in lieu of or in addition vibration.

In another aspect of the invention, the probe 230 may be equipped with a means for heating 270 such as a solid state heating element which may be regulated to provide relatively precise amounts of energy in the previously mentioned ranges that assists in softening, liquifying or melting the obstruction P via heat transfer through the tissue when the probe is placed against the tissue.

Figure 9:
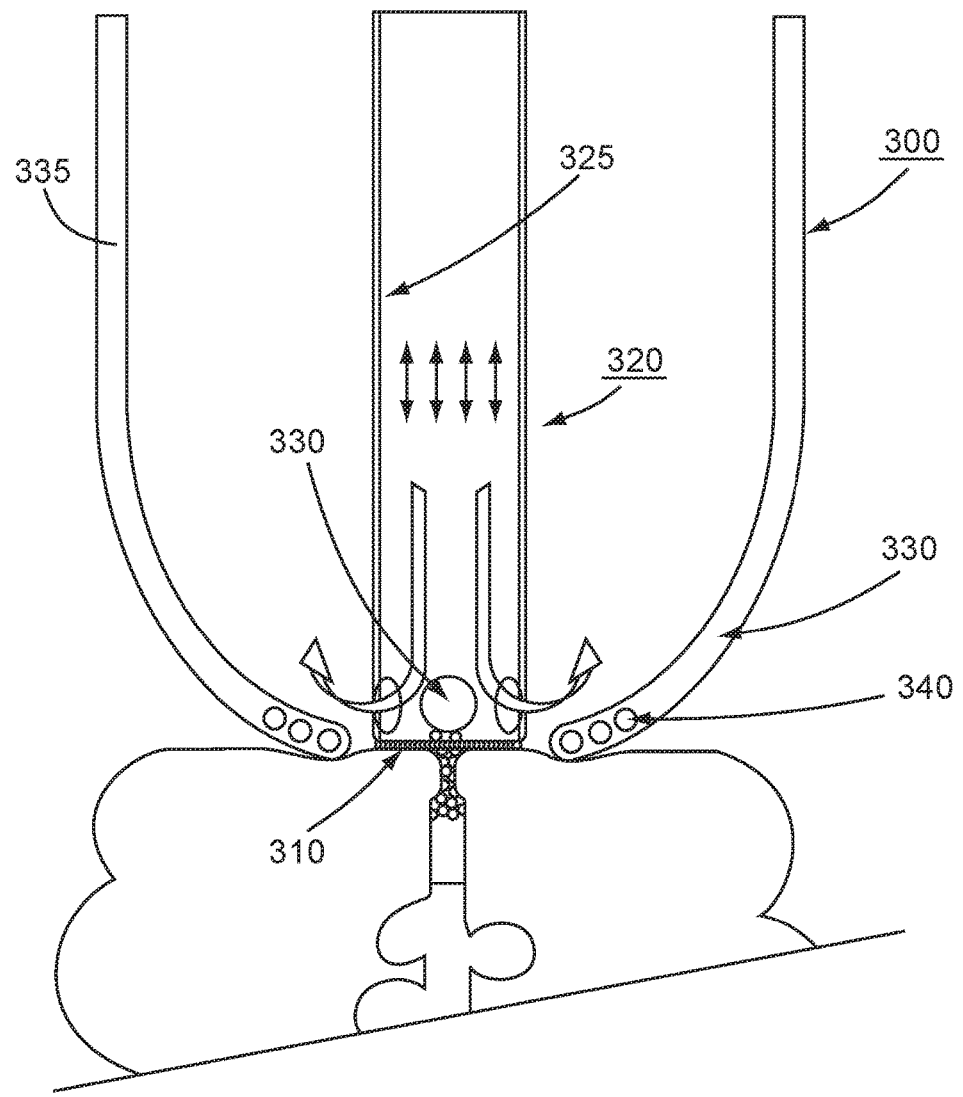
FIG. 9 is broken away side view of an alternate for clearing obstructed meibomian glands according to the present invention.

A second embodiment of the invention (FIG. 9) employs microdermabraision or exfoliation to remove any cells or cellular material that may have overgrown the gland opening. Microdermabraision is a process that was developed for use in dermatology to remove dead skin cells. As shown in FIG. 9 a probe or tip 330 is equipped with an abrasive surface 310 that is adapted to scrape the skin. The abrasive employed is usually a diamond power or other suitable material, well known to those skilled in the art. An inner tube 320 having a central bore 325 includes holes defining openings 330 through which a fluid such as air is pumped. An outer covering 335 surrounds the tube 320, but at its lower edge extends slightly lower and is spaced from the abrasive surface 310 and a space is defined between the lower ends of the respective tubes 320, 335. The outer covering is connected to aspiration, vacuum, and/or suction that operates as described herein below.

In operation, the clinician would place the abrasive tip 310 in contact over the gland orifice creating a seal between the tip and the skin. Movement of the probe 330 would cause the abrasive 310 on the bottom of the tip to separate the cells from the skin and the aspiration, suction or vacuum would extract the cellular material from the vicinity of the gland opening. In addition, depending upon the obstruction, aspiration, suction and/or vacuum alone may be sufficient to extract the obstruction.

Additional features may also be providing to the microdermabraision tip such as a heating element 340 which could be placed in the outer covering 335 near the tip. In addition, the inner tube 320 could be equipped such that ultrasonic energy could be delivered to the obstruction as discussed herein above.

Another embodiment of the invention may employ a chemical agent to clean the gland margin and to remove or exfoliate cells from the meibomian gland orifice. For example Ophthaine® or a similar pharmacological agent may be employed to assist in removing epithelial cells from over the gland orifice. A probe similar to that shown in FIG. 9 may be employed, except that the inner tube will deliver the chemical agent and the suction applied by the outer covering will be used to evacuate the used chemical agent and cellular material mixture away from the gland margin. Similarly, the heating and vibrational features discussed above may also be included.

A further embodiment of the invention may deliver vibrational and/or thermal energy to the obstruction P without contacting the gland. One potential energy source is laser light supplied by titanium, argon, krypton or microwave energy. Extraction of the obstruction would be accomplished by the means described herein above.

Figure 10A:
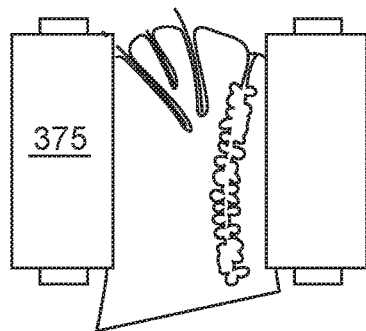
FIG. 10A is a side view of an alternate embodiment of the probe tip having rollers for clearing obstructed meibomian glands according to the present invention.
Figure 10B:
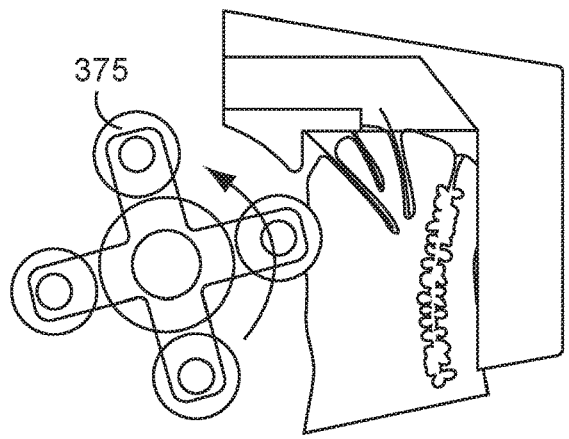
FIG. 10B is a side view of another alternate embodiment of the probe tip having rollers for clearing obstructed meibomian glands according to the present invention.
Figure 11:
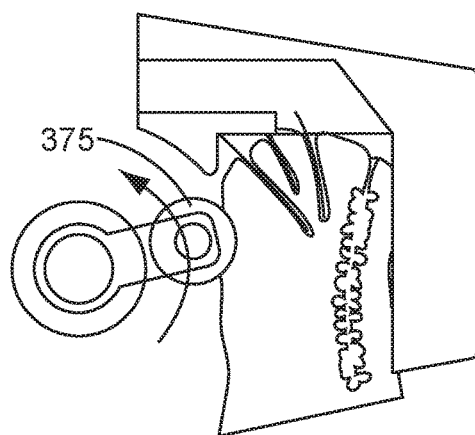
FIG. 11 is a side view of another alternate embodiment of the probe tip having rollers for clearing obstructed meibomian glands according to the present invention.

A third embodiment of the invention employs pressure applied to the tissue as shown in FIGS. 10A, 10B, and 11 by rollers (or drums) 375 which are placed in front of and/or behind the meibomian gland with the rollers applying constant regulated pressure to the meibomian glands to apply a "milking" type force to expel the obstruction to return the gland to normal secretion levels. The rollers can be connected to heat, aspiration, vacuum, and/or suction that operate as described herein.

In operation, the physician would place the rollers 375 in contact with the eyelid, either inside, outside or both. Lateral movement of the rollers 375 would cause pressure to be applied to the gland to remove the obstruction. Alternatively, aspiration, suction and/or vacuum could be applied to extract the obstruction and material from the vicinity of the gland opening. In addition, depending upon the obstruction, aspiration, suction and/or vacuum alone may be sufficient to extract the obstruction.

Additional features may also be provided to the rollers such as a regulated heating element (not shown) which could be placed in the outer covering near the tip as shown in FIG. 10A. In addition, the roller 375 could be equipped such that ultrasonic energy could be delivered to the obstruction as discussed herein above.

Figure 12:
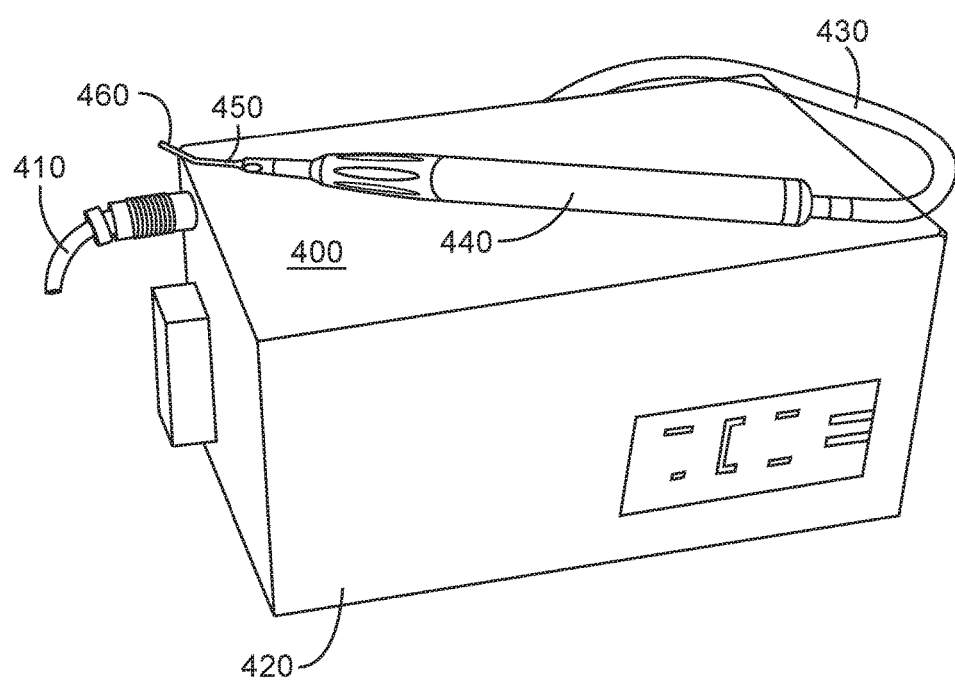
FIG. 12 is a perspective view of a suction device for clearing glands according to the present invention.

FIG. 12 illustrates a prototype hand held suction system generally indicated at 400 that was constructed. The system comprised an AC power supply 410 which powered a suction pump 420 to which tubing 430 was connected. At the opposite end of tubing 430 a probe 440 was connected. A tip 450 having a 1 mm diameter and a 200 micron orifice was attached to the end of the probe 440. The probe end 460 was curved for ergonomic access to the gland orifice. In use, the tip 450 is placed on or proximate the gland orifice and the applied vacuum is used to collect the obstruction as it exits the orifice or may alternatively be employed to assist in expression of the obstruction.

Figure 13:
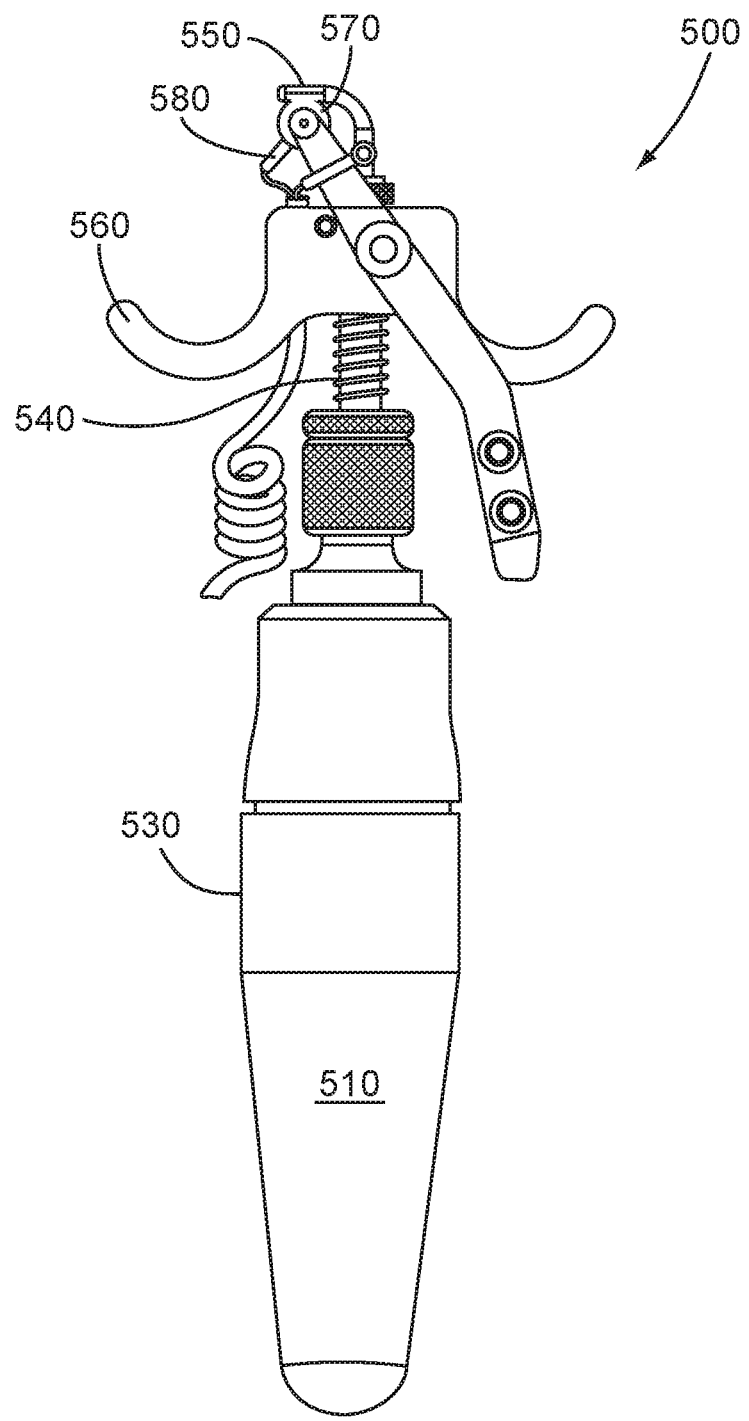
FIG. 13 is a side view of another embodiment of the apparatus for clearing meibomian glands according to the present invention.

FIG. 13 illustrates another prototype of a hand held apparatus generally indicated at 500 that was constructed. The system comprised a power supply 510 which powered an electromagnet (not shown) which was encased in a handle 530 that may be easily held by the clinician in one hand. A rod 540 is mounted for reciprocating motion to the output of the electromagnet. The throw or amount of movement of the rod 540 is 0.5 mm. At the end of rod 540 is mounted a back plate 550 which is substantially perpendicular to the axis of rod 540. Further, a lever 560 is pivotally mounted to rod 540 and operates to actuate a roller 570. A heating means or heater 580 was mounted in backplate 550. The heater 580 was also provided with an appropriate power source. In operation, the device is positioned such that the back plate 550 is positioned between the cornea and the back surface of the eye lid. The lever 560 is actuated such that the roller 570 comes into contact with the front surface of the eye lid. The arc of the roller is such that the eye lid is squeezed between the foregoing The clinician may elect to maintain the back plate and the roller under tension for a preselected period of time to soften the obstruction. Once the desired temperature has been reached, further pressure on the lever 560 will cause the roller to move from the bottom of the meibomian gland (the end away from the orifice) to the top of the gland to express the obstruction from the gland in a "milking type" motion. Thus, a repeatable regulated method for opening obstructed meibomian glands is provided.

Figure 14A:
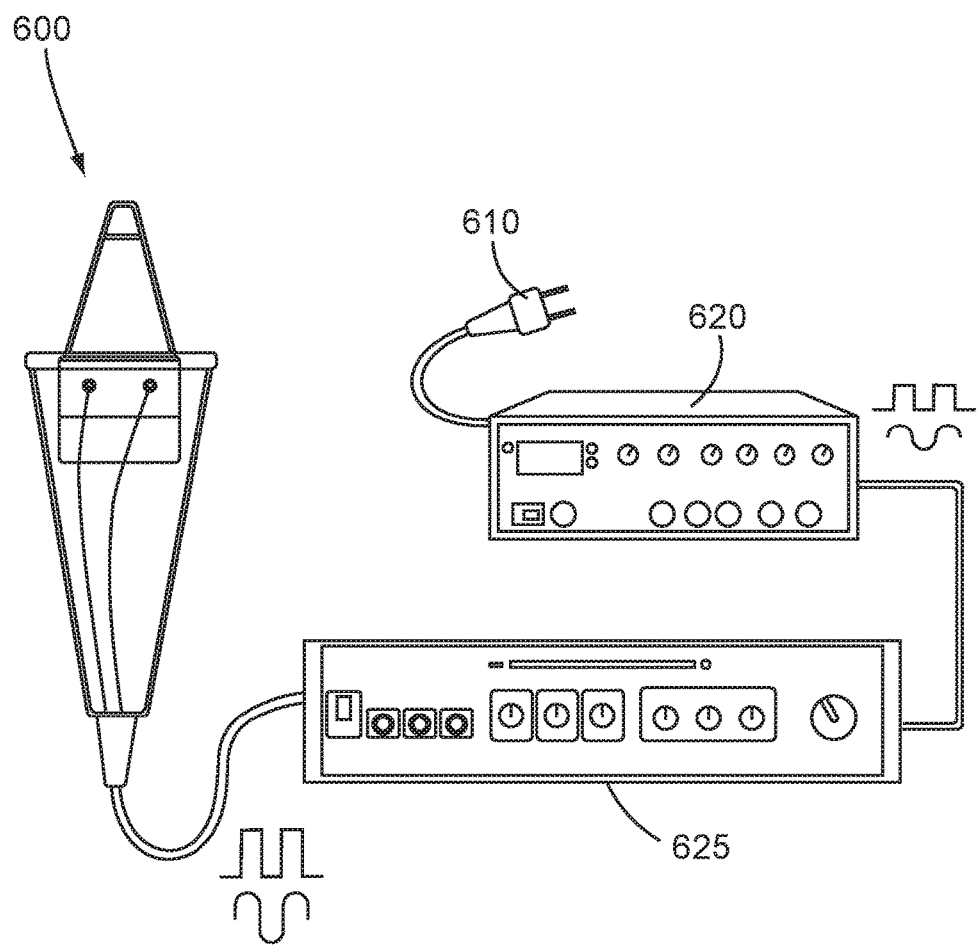
FIG. 14A is a schematic view of another embodiment of the apparatus for clearing meibomian glands according to the present invention.
Figure 14B:
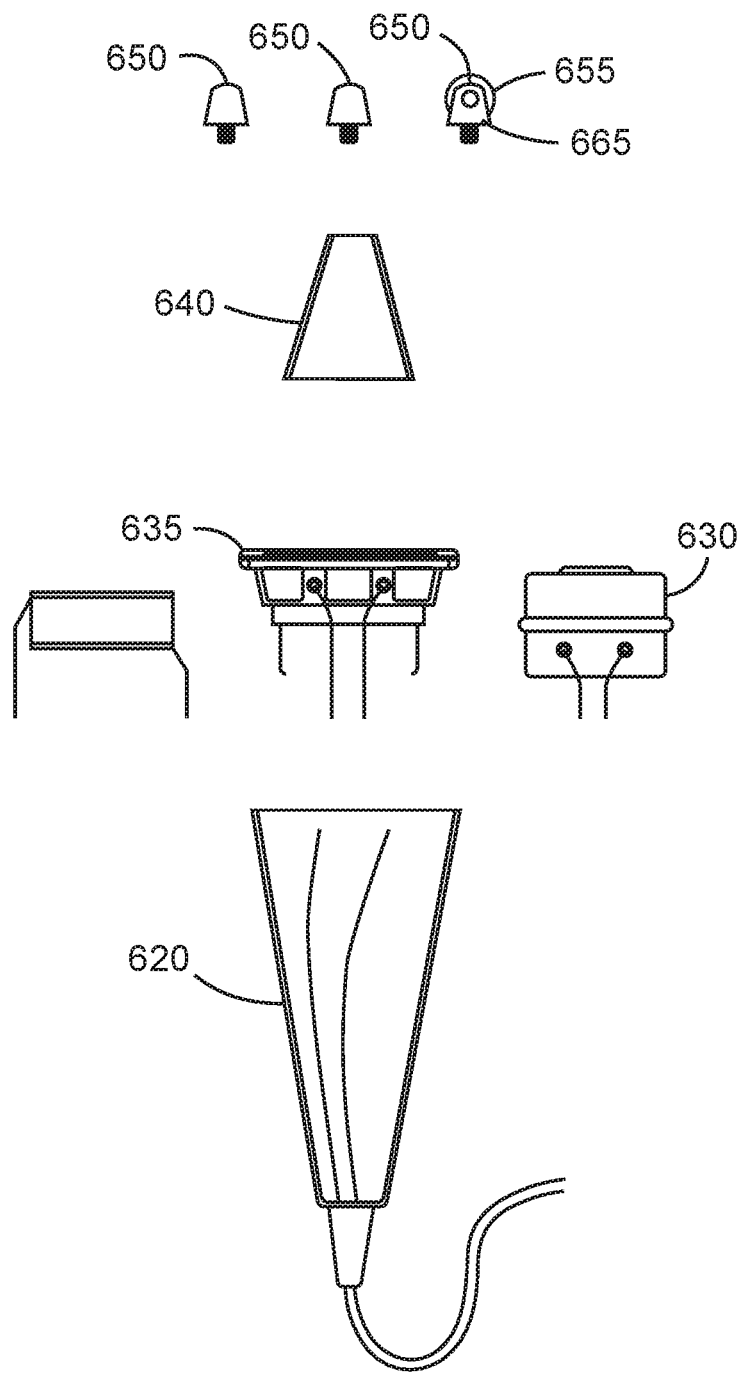
FIG. 14B is an exploded view of the hand-held probe of the embodiment of FIG. 14A.
Figure 14C:
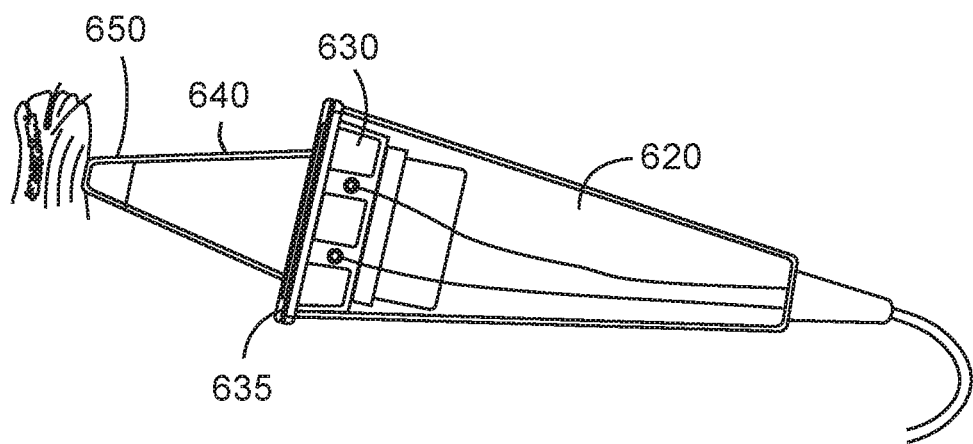
FIG. 14C is a side view of the hand-held probe of FIGS. 14A and 14B applying force to an eyelid.

The embodiment illustrated in FIGS. 14A through 14C, the present invention prototype is a hand held apparatus generally indicated at 600. The apparatus comprises a power source 610 which may be a DC source such as a battery or an AC source similar to those discussed herein above. The power source 610 resides within a housing 620. The power source 610 provides electrical current to a wave form generator 625 which powers an acoustic amplifier 630 (for example, a small audio speaker) also located within housing 620 and mounted at an ergonomic angle therein. The acoustic amplifier 630 is programmed to vibrate in a wave format at a frequency of 0 to 200 Hz at an amplitude in the range of 0.25 mm to 5 mm. Initial experiments indicate that free air amplitude of 3-4 mm at a frequency of 60 Hz to 125 Hz is well tolerated and after 10-30 seconds of application seems to impart a natural numbing effect to the eyelid/gland. Mounted in operative association atop the acoustic amplifier 630 is an annulus 635 that floats thereon and includes a cone shaped housing 640 extending perpendicularly away from the amplifier 625 that encloses the amplifier 625 The end of the housing 640 is adapted to mount a variety of tips 650. For example, the tip may comprise a roller 655 mounted for rotation in a cradle 665. Further, the tip 650 may be modified to include a regulated heating element (not shown) that acts to soften the obstruction. Other tip configurations may include a vacuum for collecting the obstruction after expression thereof from the gland and different tip configurations to apply various contact areas and resulting forces. Thus, it will be seen that the obstruction is actually subjected to a pair of forces, the first being the weight of the device itself on the gland which may be combined with additional pressure by the health care provider pressing on the gland plus the additional intermittent force delivered to the gland by the vibratory or pulsatory force of the tip 650. The first force may be a fixed constantly applied force or one that increases to a preselected maximum. Testing has indicated that use of the foregoing method, i.e., applying a first force to the meibomian gland and a second pulsatile force to the meibomian gland allows delivery of a greater quantity of energy to the obstruction while lowering the perceived pain level to the patient. It is believed that this is the result of an overall lower degree of localized nerve stimulation about the orbit. Heating the gland is also beneficial in the event softening of the obstruction is needed prior to expression thereof.

Another embodiment of the invention is shown in FIGS. 15A through 15E wherein the treatment apparatus is incorporated into a goggle-like device, termed herein as the "hydro-oculator" which is a head borne device that locates the treatment mechanism proximate the eyelids, generally indicated at 700. The hydro-oculator 700 comprises a flexible frame 705 having a headband 710 (which may be elastic) connected thereto at each end. Connected to the bottom of the frame 705 is a molded housing 720 which has an angled leg 725 which is adapted to overlie the cheek bone when the apparatus is in use. Further, an expandable fluid or gas impermeable container referred to herein as a bladder 730 is positioned within the cavity defined by the space between the housing and the lower eye lid. A pumping mechanism is provided that facilitates movement of a fluid or gas, collectively referred to herein as a "medium" (not shown), into and out of each of the respective bladders 730. According to the invention, the patient would position the hydro-oculator 700 on his or her head such that the leg 725 of molded housing 730 rests on the upper cheek bone as best shown in FIGS. 15C through 15E. The regulated heated medium is pumped into the bladders 730 causing partial expansion thereof in order to apply a pressure to the eyelids in the range of from zero to fifty pounds per square inch (50 psi). The bladder containing the heated medium (a water based solution being preferred) is positioned on the eyelids over the meibomian glands for a preselected period of time (up to thirty minutes) to soften the obstruction. It is desirable to place the heat source in direct contact with the eyelids which thereby transmits thermal energy to the meibomian glands, in contrast to the prior art which heats a confined space in front of the open eye where heat could be transmitted to the ocular bulbi structures such as the crystalline lens which introduces the possibility of cataract formation. Thereafter, the bladder is slowly expanded to a preselected maximum such that the force on the gland increases from the bottom up to the top or orifice end of the gland such that the obstruction is expressed therefrom in a "milking" type of action. Milking may be applied at a preselected frequency between zero and five hertz (0-5 Hz) and for a preselected period of time, usually not more than thirty minutes. In addition, the medium may be "pulsed", i.e., milkingly moved into and out of the bladder to further facilitate expression of the obstruction from the gland. Pulsing may also be achieved by providing an external force to the bladder and transmitting the force through the fluid into the gland. Pulsing may be applied at a preselected frequency between zero and one hundred hertz (0-100 Hz) for a preselected period time, usually not more than thirty (30) minutes. A chemical or pharmacological agent may be inserted into the meibomian gland to assist in softening the obstruction and any of the extraction modalities mentioned above may be further employed to assist in removing the obstruction.

Another embodiment of the invention may employ a chemical agent or compound to clean the glandular margin to remove or exfoliate cells from the gland orifice. A probe similar to that shown in FIG. 9 may be employed, except that the outer drum or roller will deliver the chemical agent and the suction applied by the outer covering will be used to evacuate the used chemical agent and cellular material mixture away from the gland margin. Similarly, the heating and vibrational features discussed above may also be included.

A further embodiment of the invention may deliver vibrational and/or thermal energy to the obstruction P without contacting the gland. One potential energy source is laser light supplied by a titanium-sapphire, argon, krypton, RF energy or microwave energy. Extraction of the obstruction would be accomplished by the means described herein above.

Another embodiment of the invention employs the use of chemical or pharmacological agents to open or dilate the gland and gland orifice wherein the obstruction naturally is expressed and returns the normal secretions of the gland. Alternatively, the chemical or pharmaceutical agent would be used to soften or breakup the obstruction with such obstruction being expressed with the use of devices as defined above or combinations thereof. Chemical or pharmacological agents may also be used in connection with the device for post treatment. Once the glands have been opened then chemical or pharmacological agents may be used to enhance the normal production or secretion to maintain the glands in its unblocked state.

Dilation of the meibomian gland channel and orifice may also be employed to loosen or free the obstruction from the gland walls. Dilation may be accomplished by chemical, pharmacological, or mechanical means.

Stimulation of the meibomian gland may also be employed in conjunction with the other modalities discussed above to loosen or fracture the obstruction.

While certain illustrative embodiments have been described, it is evident that many alternatives, modifications, permutations and variations will become apparent to those skilled in the art in light of the foregoing description.

What is claimed is:
1. A method of treating meibomian glands having a meibomian gland channel and a meibomian gland orifice at a top of the meibomian gland channel, comprising:
    applying regulated heat to an eyelid containing the meibomian glands to reach a temperature adequate to melt at least one obstruction within at least one meibomian gland and place the at least one obstruction in a melted state;

maintaining the regulated heat for a time period adequate to melt the at least one obstruction and place the at least one obstruction in the melted state; and positioning a pressure application device into direct contact with the eyelid and applying a pressure with the pressure application device over a substantial portion of the eyelid to express the at least one obstruction from the at least one meibomian gland.

2. The method according to claim 1, wherein the at least one obstruction is located within the meibomian gland channel, the applying and the maintaining the regulated heat comprises applying and maintaining the regulated heat to place the at least one obstruction located in the meibomian gland channel in a melted state, and the applying the pressure with the pressure application device comprises applying a pressure to the meibomian gland channel to express the at least one obstruction from within the meibomian gland channel through the meibomian gland orifice.

3. The method according to claim 2, wherein the applying the pressure further comprises milkingly expressing the at least one obstruction located within the meibomian gland channel from within the meibomian gland channel through the meibomian gland orifice of one or more of the meibomian glands.

4. The method according to claim 1, wherein the time period comprises approximately 10 to 60 minutes.

5. The method according to claim 1, wherein the pressure application device comprises a heated instrument.

6. The method according to claim 1, wherein the temperature reaches approximately 45 degrees Celsius.

7. The method according to claim 1, wherein the temperature reaches between approximately 44 and 47 degrees Celsius.

8. The method according to claim 1, wherein the temperature is at least 37 degrees Celsius.

9. The method according to claim 1, wherein the applying the pressure is carried out within 3 minutes after an end of the time period.

10. The method according to claim 1, further comprising subsequently treating at least one meibomian gland by use of a pharmacological agent.

11. The method according to claim 1, further comprising repeating the applying and maintaining of the regulated heat after a time interval to maintain flow of fluids from the meibomian glands.

12. The method according to claim 11, further comprising repeating the applying the pressure with the pressure application device at the time interval to maintain the flow of fluids from the meibomian glands.

13. The method according to claim 1, wherein the applying the pressure further comprises applying constant compressive force to the eyelid.

14. The method according to claim 1 further comprising applying vibratory stimulation to the eyelid.

15. The method according to claim 1, further comprising applying a pulsating compressive force to the eyelid.

* * * * *